(12) United States Patent
Serafinowski et al.

(10) Patent No.: US 7,301,049 B2
(45) Date of Patent: Nov. 27, 2007

(54) PHOTOLABILE ESTERS AND THEIR USES

(75) Inventors: Pawel Jerzy Serafinowski, Orpington (GB); Peter Bryan Garland, Bosham (GB)

(73) Assignee: The Institute of Cancer Research, London (GB)

( * ) Notice: Subject to any disclaimer, the term of this patent is extended or adjusted under 35 U.S.C. 154(b) by 329 days.

(21) Appl. No.: 10/481,707

(22) PCT Filed: Jun. 21, 2002

(86) PCT No.: PCT/GB02/02896

§ 371 (c)(1),
(2), (4) Date: Jul. 16, 2004

(87) PCT Pub. No.: WO03/000644

PCT Pub. Date: Jan. 3, 2003

(65) Prior Publication Data

US 2004/0242653 A1    Dec. 2, 2004

(30) Foreign Application Priority Data

Jun. 21, 2001  (GB)  .................... 0115231.3
Sep. 21, 2001  (GB)  .................... 0122760.2

(51) Int. Cl.
*C07C 309/00*  (2006.01)
(52) U.S. Cl. ........................................ 562/73
(58) Field of Classification Search .................. 562/73
See application file for complete search history.

(56) References Cited

FOREIGN PATENT DOCUMENTS

| | | |
|---|---|---|
| DE | 22 07 574 A | 8/1973 |
| EP | 0 046 028 A | 2/1982 |
| EP | 0 046 083 A | 2/1982 |
| EP | 0 077 961 A | 5/1983 |
| EP | 0 476 865 A1 | 3/1992 |
| JP | 2001 190143 A | 4/2001 |
| WO | WO 99/41007 A | 8/1999 |
| WO | WO 00/66259 A | 11/2000 |
| WO | WO 01/32720 A1 | 5/2001 |

OTHER PUBLICATIONS

Hiroyoshi Kamogawa, Seichu Nin and Manabu Horiuchi Polymers of 4-vinyl-2'-nitrodiphenylmethyl carboxylates capable of releasing functional acid by light Reactive Polymers, 18 (1992) 125-131.*
Hiroyoshi Kamogawa, Seichu Nin and Manabu Horiuchi Reactive Polymers, 18 (1992) 125-131.*
Kamogawa, H., et al., "Polymers of 4-vinyl-2'-nitrodiphenylmethyl carboxylates capable of releasing functional acid by light," Reactive Polymers, 18:125-131, (1992).
Houlihan, F.M., "The Photo and Thermo Chemistry of Select 2,6-Dinitrobenzyl Esters in Polymer Matrices: Studies Pertaining to Chemical Amplification and Imaging", vol. 61: 296-301 (1989).

Gao, et al. "Oligonucleotide Synthesis Using Solution Photogenerated Acids", J. Am. Chem. Soc. vol. 120: 12698-12699 (1998).
Gao, X., et al., "A flexible light-directed DNA chip synthesis gated by deprotection using solution photogenerated acids", vol. 29(22): 4744-4750 (2001).
Koshi, K., et al., "The Synthesis of 2,3-Dimethoxy-5-methyl-p-benzoquinone and Related Compounds", Chem. Pharm. Bull. 16(12): 2343-2350 (1968).
Cunico, R.F., "Aminooxycarbene behavior of a carbamoylsilane", Tetrahedron Letters, 42: 2931-2932 (2001).
Corrie, J.E.T., et al., Synthesis and Absolute Stereochemistry of the Two Diasatereoisomers of $P^3$-1-(2-Nitrophenyl)ethyl Adenosine Triphosphate ('Caged' ATP), J. Chem. Soc. Perkin Trans. 1: 1015-1019 (1992).
Seebach, D., et al., "Entantioselective addition of Aryl Groups to Aromatic Aldehydes Using Chiral Aryltitanium Binaphtol Derivatives", Chem. Ber. 118: 3673-3682 (1985); See English Abstract.
Puckowski, R.T., et al., "The Preparation and Reactions of Some Optically Active Substituted Benzhydrols", J. Chem. Soc. 3555-3564 (1959).
Batey, R.A., et al., "Potassium Alkenyl- and Aryltrifluoroborates: Stable and Efficient Agents for Rhodium-Catalyzed Addition to Aldehydes and Enones", Organic Letters 1(10): 1683-1686 (1999).
Miyashita, K., et al., "Novel indole-ring formation by thermolysis of 2-(N-acylamino)- benzylphosphonium salts. Effective synthesis of 2-trifluoromethyl-indoles", J. Chem., Soc., Perkin Trans., 1: 1261-1268 (1996).
Effenberger, F., et al., Hydroxyalkylation, Acylation, Formylation, and Carboxylation of 2-Nitro- and 2-Chloro-1-(trimethylsily)benzene. Chem. Ber. 118: 3900-3914 (1985); See English Abstract.
Smirnov, S.K., et al., "4,5-Dimethoxy-2-nitrobenzhydrol" Molecules 4: M113 (1999).
Waksmundzka-Hajnos, M., "Chromatographic separation of nitrophenones and their reduced derivatives on thin layers of polar adsorbents", Acta Chromatographica No. 7 p. 159-171 (1997).

(Continued)

*Primary Examiner*—Samuel A Barts
*Assistant Examiner*—Lalitha Nagubandi
(74) *Attorney, Agent, or Firm*—Dann, Dorfman, Herrell and Skillman, P.C.; Patrick J. Hagan

(57) ABSTRACT

Compounds which are capable of generating acid on photolysis are disclosed, and the uses of these compounds, especially for deprotecting the termini of nucleic acid molecules or peptides during synthesis of arrays. The compounds described herein may be employed in the detritylation of 5'-O-dimethoxytrityl (DMT) protected nucleotides by photolysing the compounds to generate an acid capable of removing the DMT group allowing oligonucleotide arrays to be synthesised using readily available 5'-O-DMT-nucleoside-3'-O-phosphoramidite monomers conventionally used in solid phase nucleic acid synthesis. A method of avoiding the effects of stray light in projection lithography techniques is also disclosed.

15 Claims, 2 Drawing Sheets

OTHER PUBLICATIONS

Walser, A., et al., "A cinnonline 2-oxide from 2-nitrosobenzophenone", J. Heterocyclic Chem., 13(4): 907-908 (1976).

Barzynski, H., et al., "Zur Photolyse von makromolekularen o-Nitrobenzylderivaten" Die Angewandte Makromolekulare Chemie 93: 131-141 (1981); See English Abstract.

Colominas, C., et al., "Conformational folding induced by II-II interaction in a series of flexible dyads consisting of isomeric mesoporphyrin nitrobenzyl esters", J. Chem. Soc. Perkin Trans., 2: 997-1004 (1996).

Yip, R.W., et al., "Photochemistry of the o-Nitrobenzyl System in Solution: Evidence for Singlet State Intramolecular Hydrogen Abstraction", J. Phys. Chem., 89: 5328-5330 (1985).

Reichmanis, E., et al., "o-Nitrobenzyl Photochemistry: Solution vs. Solid-State Behavior", J. Of Polymer Science 23: 1-8 (1985).

Wharton, C.W., et al., "Use of Caged Compounds in Studies of Bioelectronic Imaging and Pattern Recognition", Methods in Enzymology, vol. 291: 245-250, G. Marriott editor of "Caged Compounds" (1998).

Paul, C.H., et al., "Acid binding and detritylation during oligonucleotide synthesis", Nucleic Acid Research, vol. 24: 3048-3052 (1996).

Cummings, R.T., et al., "Photoactivable fluorophores. 1. Synthesis and photoactivation of o-Nitrobenzyl-quenched fluorescent carbamates." Tetrahedron Letters, vol. 29: 65-68 (1988).

Walker, J.W., et al., "Photolabile 1-(2-Nitrophenyl)ethyl Phosphate Esters of Adenine Nucleotide Analogues. Synthesis and Mechanism of Photolysis", J. Am. Chem. Soc. vol. 110: 7170-7177 (1988).

Kim, S., et al., "Intramolecular Nucleophilic Participation. VIII. Acetolysis of o- and ρ-Nitro- and o and ρ-Carbophenoxybenzhydryl Bromides" J. Am. Chem. Soc. vol. 92: p. 5452-5456 (1970).

Cocker, W., et al., "A Preparation of m-Dimethylaminobenzaldehyde", J. Chem. Soc., p. 751-753 (1938).

LeProust, E., et al., "Digital Light-Directed Synthesis. A Microarray Platform That Permits Rapid Reaction Optimization on a Combinatorial Basis", J. Comb. Chem., vol. 2: 349-354 (2000).

Pease, A.C., et al., "Light-generated oligonucleotide arrays for rapid DNA sequence analysis", Proc. Natl. Acad. Sci. USA, vol. 91: 5022-5026 (1994).

McGall, G.H., et al., "High-Density Oligonucleotide Probe Arrays", Advances in Nucleic Acid and Protein Analyses, Manipulation, and Sequencing, Editors: P.A. Limbach, et al., Proceedings of SPIE vol. 3926: 1017-2661 (2000).

Beecher, J.E., et al., "Chemically Amplified Photolithography for the Fabrication of High Density Oligonucleotide Arrays", Polymeric Materials Sci. Eng. (Washington) 76, p. 597-598 (1997).

Eckstein, F., Editor, "Oligonucleotides and Analogues: a practical approach", IRL Press Ltd., Oxford, NY, Tokyo, p. vii, xxiii-xxiv, 1-24 (1991).

Caruthers, M.H., "Chemical Synthesis of DNA and DNA Analogues", Acc. Chem. Res., 24: 278-284 (1991).

Beaucage, S.L., et al., "Advances in the Synthesis of Oligonucleotides by the Phosphoramidite Approach", Tetrahedron vol. 48: p. 2223-2311 (1992).

Fodor, S.P.A., et al., "Light-Directed, Spatially Addressable Parallel Chemical Synthesis", Science vol. 251: p. 767-773 (1991).

Singh-Gasson, S., et al., "Maskless fabrication of light-directed oligonucleotide microarrays using a digital micromirror array", Nature Biotech., vol. 17, p. 947-978 (1999).

Garner, H.R., Abstracts of Cambridge Healthtech Institute Conference "Lab Chips and Microarrays for Biotechnological Applications", Zurich, Jan. 13-15, 1999.

Stähler, P.F., Abstract of IBC Conference "Chips to Hits", Philadelphia, Nov. 6-9, 2000.

Hornbeck, L.J., "From cathode rays to digital micromirrors: A history of electronic projection display technology", Texas Instruments Technical Journal, vol. 15 July-Sept. p. 7-46 (1998) (Obtainable at www.ti.com/dlp).

Bevington, "Chapter Three: Distributions" from "Data Reduction and Error Analysis for the Physical Sciences", p. 27-37 McGraw-Hill Book Comany, NY (1969).

Temsamani, J., et al., "Sequence identity of the n—1 product of a synthetic oligonucleotide", Nucleic Acids Research, vol. 23: 1841-1844 (1995).

Fearon, K.L., et al., "Investigation of the 'n—1' impurity in phosphorothioate oligodeoxynucleotides synthesized by the solid-phase β-cyanoethyl phosphoramidite method using stepwise sulfurization", Nucleic Acids Research, vol. 23: p. 2754-2761 (1995).

[Abstract] Slotta and Lauersen, "2-nitroveratic acid: Process for the synthesis of 2-nitro-veratric acid from vanillin (3-methoxy-4-hydroxbenzaldehyde", Journal für praktische Chemie N.F., p. 220-228 (1934). (1 page abstract enclosed).

* cited by examiner

Figure 1. Graph of $\log_{10}$(contrast ratio) and the % of oligonucleotide chains ( of length N=10, 20 & 30) free of stray light induced insertions when synthesised using direct 5'-OH photodeprotection and illumination for 10 half-times.

Fig. 2. Effects of stray light on photodirected oligonucleotide synthesis. HPLC Recordings. Absorbance at 260nm against retention time.
A. Photodirected $T_5$ synthesis. 1% stray light cycles, alternating with full illumination cycles.
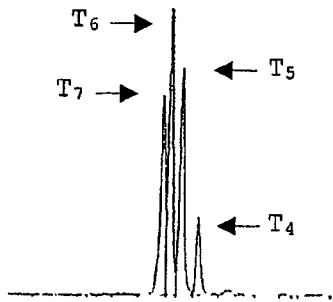
B. As A but 0.5mM 1-octylamine added with the photoacid generator
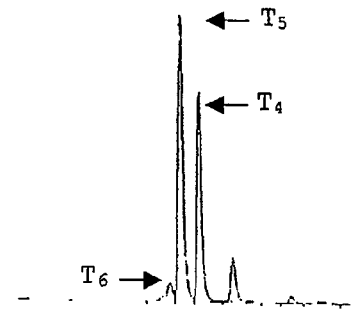
C. Conventional synthesis of $T_6$. Not photodirected.
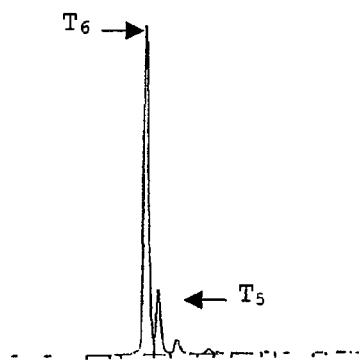

PHOTOLABILE ESTERS AND THEIR USES

FIELD OF THE INVENTION

The present invention relates to photolabile esters and more especially to photolabile esters which generate acid on photolysis. The present invention further relates to the uses of these compounds, in particular for removing protecting groups in the synthesis of oligonucleotides or peptides, e.g. in the construction of microarrays.

BACKGROUND OF THE INVENTION

Photolithography and direct photochemical unblocking are techniques used in microarray technology to build up arrays of oligonucleotides or peptides binding agents at defined locations on solid support. Although this approach is employed to generate arrays for use in some analytical applications based on DNA-hybridisation, the high cost of photolithographic masks, the use of non-commercial photolabile phosphoramidite monomers and problems with quantitative, direct photochemical unblocking lead to very expensive and often poor quality microarrays[30].

One attempt to solve these problems is based on so-called chemical amplification. This technique is borrowed from the electronics industry, and uses a combination of photochemically and thermally generated acid production at desired sites on an array surface covered with a diffusion-limiting polymeric film[31]. However, the need to use strong acids such as benzenesulphonic acid in the key photodirected step, while acceptable in the production of intergrated circuits, makes application of this approach with acid labile purine nucleosides difficult[32,33]. There have been attempts to overcome these problems by designing new photoacid generating compounds, but on the whole, these attempts have not been successful. By way of example, Le Proust et al[28] and Gao et al[27] have employed photolabile hexafluoroantimonates in the synthesis of oligonucleotides in solution (see also WO99/41007). However, these photoacid generators involve the release of free radicals which can result in undesirable side reactions such as blockage of 5'-OH group.

Reichmannis et al[34] described 2-nitrobenzyl esters which photolyse to produce trimethylacetic acid, and more particularly the mechanism of this reaction and its yield, both in solution and in a polymer matrix. WO00/66259 describes the use of photoactivated reagents which when activated are capable of removing protecting groups at the termini of substrates being synthesised on a solid phase. The application suggests the use of triarylsulphonium hexafluorantimonates, triarylsulphonium hexafluorophosphates, 2,1,4-diazonapthoquinone sulphonates and perhalogenated traiazines. In one example, 1-[2-nitrophenyl]ethyl-1-trichloroacetate is irradiated with UV light to generate trichloroacetic acid for removing protecting 5'-dimethoxytrityl groups from oligonucleotide substrates.

The actual fabrication of arrays of binding agents and in particular oligonucleotide or peptide arrays is an area of intense interest in the art. The chemical synthesis of binding agents such as oligonucleotides is well known. The most commonly used method is a solid phase synthesis using controlled porosity glass or equivalent material as the support. Stepwise extension of an oligonucleotide attached via a linker molecule to the support occurs by addition of one nucleotide at a time. Attachment to the linker is commonly through the oligonucleotide-3'-OH, with chain extension therefore at the oligonucleotide-5'-OH. Because of the stepwise nature of the process, satisfactory synthesis of oligonucleotides of commonly desired chain lengths of 20 or more nucleotides requires a high stepwise yield. The overall yield of an N-mer synthesised with a stepwise yield of Y is $Y^N$, and diminishes rapidly once Y falls beneath about 0.95. After completion of synthesis the oligonucleotide is cleaved from the support and purified prior to use. Caruthers[35] and Beaucage & Iyer[36] have written detailed reviews of oligonucleotide synthesis methods.

Typically, each new oligonucleotide monomer is added to a growing oligonucleotide as a modified nucleotide substituted at its 5'-OH position with a 4,4'-dimethoxytrityl group, and a beta-cyanoethyl-phosphoramidite at its 3'-OH position. Synthesis starts by coupling the first nucleotide through its 3'-OH group to the terminal hydroxyl group of a linker molecule attached to a solid support. Any unreacted terminal OH groups are then blocked with acetic anhydride, and the trivalent phosphite is oxidised to pentavalent phosphate. The dimethoxytrityl group is then removed with acid from the 5'-OH position of the first nucleotide, which can then react with the next nucleotide phosphoramidite to be added. The cycle of steps is then repeated until the desired chain length has been synthesised. Finally, alkali treatment is used to remove N-protective groups and also to cleave an alkali-labile bond in the linker, thereby releasing the oligonucleotide which may then be purified.

In prior art solid phase synthesis methods, removal of DMT, or detritylation, is effected with di- or trichloroacetic acid according to equation (1). Stronger acids cause chain breakage by depurination. It should be noted that protons are reagents, not catalysts, in the detritylation reaction, and are consumed with a stoichiometry of 1 proton per $DMT^+$ cation released, as in equation (1):

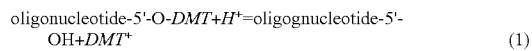

oligonucleotide-5'-O-*DMT*+$H^+$=oligognucleotide-5'-OH+*DMT*$^+$  (1)

The repetitive cycle of steps in the synthesis of oligonucleotide, or indeed peptide, lends itself to automation, and a variety of commercially available instruments have been developed for that purpose. The availability of synthetic oligonucleotides has led to the development of arrays of oligonucleotides on paper or other polymeric sheets, fabric or glass, allowing multiple hybridisation reactions to be carried out in parallel.

Early descriptions of oligonucleotide arrays were from academic laboratories and the array densities achieved were modest. Construction methods define three classes of array, namely (a) arrays printed from pre-synthesised oligonucleotides, (b) arrays synthesised in situ by reagent printing and (c) arrays synthesised in situ by a photodirected method.

The printing methods create array elements at a modest density, up to 5,000/cm², with each element having a diameter of about 0.1 mm and separated from its neighbours by a similar distance and possibly an additional physical barrier to prevent reagents that should be constrained to selected elements from spreading to adjacent elements. Photolithographic methods currently achieve much higher densities (160,000/cm²), with the potential for even higher (10⁶/cm²).

Photodirected synthesis of oligonucleotides in arrays was first described in 1991 by Fodor et al[37]. The main technical innovation was to replace the conventional acid-removable dimethoxytrityl blocking group at the oligonucleotide 5'-OH with a group that was photo-removable. The array elements at which groups would be unprotected, and therefore reactive with whichever A, C, G or T-deoxyribonucleotide-3'-O-phosphoramidite was subsequently applied, were determined by patterned illumination of the array surface. Proximity or contact photolithography is needed to minimise stray light, and requires numerous high precision physical masks (metal on glass or quartz), with the result that this technology has the significant disadvantages of high cost and low flexibility.

In the photodirected method for making arrays, the synthesis consists of a cycle of steps that adds a nucleotide at each chain length to photoselected array elements. The cycle is used four times (once each for A, C, G & T) to extend the length of the array by one nucleotide, and 4N times to make an array of N-mers. The first four cycles couple monomer to a linker attached to the glass or other solid surface. The linker has an aliphatic —OH group at its free end. All subsequent cycles couple monomer to oligonucleotide 5'-OH. The sequence of actions in the photodirected synthesis of an oligonucleotide array, using nucleotide monomers with photolabile protection of the 5'-OH group is given in Table 1.

The use of contact or close proximity photolithography uses masks of metal on glass or quartz. The transmission of light through the metallised areas of the mask is $10^{-5}$ of that transmitted through the clear (non-metallised) areas (Pease et al[29]). In other words, the contrast ratio of metal on glass masks is $10^5$. The associated intensity level of stray light is negligible in the context of photodirected synthesis of oligonucleotide arrays. However, the masks are expensive, and the number needed is large (100 for a 25-mer array), making this method of fabricating arrays unsuitable for use outside an expensively equipped industrial environment.

To overcome this drawback of expense and inflexibility, several groups (Singh-Gasson et al[38], Garner[39] and Staehler[40]) have reported the use of projection photolithography using Digital Micromirror Device (DMD: Hornbeck[41]) projectors) in association with photosensitive blocking groups of the oligonucleotide-5'-OH group. The aim was to avoid the cost and inflexibility of metal-on-glass physical masks by replacing them with programmable masks in silico that determine the patterned output of a light projector. LeProust et al[28] have also used a DMD projector, but used photoacid generation to deprotect the tritylated oligonucleotide-5'-OH group.

Furthermore, despite the work described above, it remains a problem in the art in generating acid for in situ deprotection of oligonucleotides.

SUMMARY OF THE INVENTION

Broadly, the present invention relates to compounds which are capable of generating acid on photolysis, and to the uses of these compounds, especially for deprotecting the termini of nucleic acid molecules or peptides during synthesis. Thus, for example, the compounds described herein can be employed in the detritylation of 5'-O-dimethoxytrityl (DMT) protected nucleotides by photolysing the compounds to generate an acid capable of removing the DMT group. This means that the present invention has the significant advantage of permitting chemistry to be used for the synthesis of oligonucleotide arrays which employs commercially available 5'-O-DMT-nucleoside-3'-O-phosphoramidite monomers conventionally used in solid phase nucleic acid synthesis[35,36], but critically adapts this robust chemistry so that it employs a photoacid generation to effect detritylation reactions at specific locations (elements) of an array of locations on a surface.

Further, unlike many prior art approaches for synthesising microarrays, the acids generated by photolysis of the compounds of the invention balance the requirements of being sufficiently strong to ensure that the deprotection step proceeds in a rapid manner, e.g. the reaction requires only thirty seconds or so, and does not lead to significant degradation of acid labile purine nucleosides. Preferred compounds of the invention also have the advantage that they have satisfactory extinction coefficients, e.g. 3500 $cm.M^{-1}$, undergo efficient photolysis, e.g. with a quantum yield of c. 0.4, and lead to only one UV absorbing product when analysed by HPLC and TLC. Further, the work described herein demonstrates quantitative production of acid ($H^+$) and that the compounds were stable and easy to work with provided that simple precautions were taken to avoid ambient UV light.

The work also predicts errors in oligonucleotide array synthesis caused by stray light at levels characteristic of maskless projection[38-41] using computer controlled DMA's, and identifies a method of ameliorating or preventing such errors in those cases where photodirected synthesis is provided by photoacid or photobase generation.

Accordingly, in a first aspect, the present invention provides a compound represented by the formula:

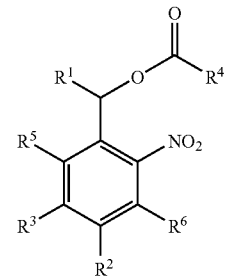

wherein:
$R^1$ is selected from hydrogen, aryl or substituted aryl, aryloxy or substituted aryloxy, or an unsubstituted or substituted heterocyclic group;

$R^2$ is selected from hydrogen, halogen, alkyl or substituted alkyl, alkoxy or substituted alkoxy, aryl or substituted aryl, aryloxy or substituted aryloxy, amino or substituted amino, or a nitro group;

$R^3$ is selected from hydrogen, alkoxy or substituted alkoxy, aryl or substituted aryl, aryloxy or substituted aryloxy, amino or substituted amino, or an unsubstituted or substituted heterocyclic group;

$R^4$ is an alkyl group substituted with one or more halogen substituents, such as $ClCH_2$, $Cl_2CH$, $Cl_3C$ or $F_3C$;

$R^5$ is selected from hydrogen, halogen, alkyl or substituted alkyl, alkoxy or substituted alkoxy, aryl or substituted aryl, aryloxy or substituted aryloxy, amino or substituted amino, a nitro group or an unsubstituted or substituted heterocyclic group; and, $R^6$ is selected from hydrogen, halogen, alkyl or substituted alkyl, alkoxy or substituted alkoxy, aryl or substituted aryl, aryloxy or substituted aryloxy, or amino or substituted amino, or an unsubstituted or substituted heterocyclic group.

In the above definitions, preferred substituents are $C_{1-10}$, and more preferably $C_{1-5}$, and may be straight chain, branched, cyclic or heterocyclic. Examples of groups that may be included in substituted functional groups, as defined above, include halogen (F, Cl, Br or I), alkyl or substituted alkyl, alkoxy or substituted alkoxy, aryl (Ar) or substituted aryl, $N_2$, CN, COOR, where R is hydrogen, halogen or an alkyl group, and unsubstituted or substituted heterocyclic groups. Heterocyclic groups include those with one or more heteroatoms (e.g. N, O or S) in a saturated, unsaturated or aryl ring system, e.g. a heterocyclic group may comprise one or two nitrogen atom in a five or six membered ring or one oxygen atom in a five or six membered ring.

Examples of preferred compounds of the invention include those in which:

$R^1$ is a phenyl or alkoxy substituted phenyl group, more preferably a 3-alkoxy substituted phenyl group, or hydrogen; and/or, $R^2$ is hydrogen or an alkoxy group; and/or, $R^3$ is hydrogen or an alkoxy group; and/or, $R^4$ is $ClCH_2$, $Cl_2CH$, $Cl_3C$ or $F_3C$; and/or, $R^5$ is hydrogen or a nitro group; and/or $R^6$ is hydrogen.

Preferred compounds of the invention include compounds 31-44 as defined below. Especially preferred compounds are esters 39 and 40, and compounds 43 and 44, which have the useful property of being sensitive to visible light.

In a further aspect, the present invention provides the use of a compound as defined herein for the synthesis of a nucleic acid molecule or peptide, wherein the compound is photolysed to produce a halogen substituted carboxylic acid capable of removing a protecting group from the terminus of the nucleic acid molecule or peptide, thereby to make it reactive to chain extension by nucleosides or amino acids.

In a preferred embodiment, the free acid generated by the photolysis of the compounds of the invention is capable of removing a 5'-O-dimethoxytrityl (DMT) protecting group present on the 5' end of a nucleic acid molecule or peptide. While the compounds can be employed in the synthesis of nucleic acid molecules of any size starting from a linker molecule attached to a solid phase and carrying a DMT-blocked hydroxyl group at its free end or a single DMT-protected nucleotide, it is particularly useful for the synthesis of oligonucleotides in the production of microarrays as it allows the microarrays to be synthesised using readily available 5-O'-DMT protected nucleosides. This helps to ameliorate the problems associated with prior art techniques which require specially synthesised monomers or else generate acids which are unsuitable for the deprotection reaction, e.g. because they degrade the nucleosides within the growing oligonucleotide chain, nucleoside monomers or undergo side reactions.

In a further aspect, the present invention provides a method of synthesizing a nucleic acid molecule or peptide on a solid support, the method comprising:

(a) bringing a nucleic acid molecule or peptide having a protected terminus into contact with a compound as defined herein;

(b) photolysing the compound to produce a halogen substituted carboxylic acid capable of removing the protecting group from the end of the nucleic acid molecule or peptide;

(c) contacting the deprotected nucleic acid molecule or peptide with nucleosides or amino acids, so that the 5' end of the nucleic acid molecule or peptide reacts with a nucleoside or amino acid; and (d) repeating steps (a) to (c) until the synthesis of the nucleic acid molecule or peptide is complete.

Preferably, the compounds are used in the synthesis of a plurality of oligonucleotides or peptides, e.g. in the formation of an array having a plurality of locations (elements) at which oligonucleotides or peptides of a given sequence are synthesized. In this method, preferably the compounds are used in a photodirected method of synthesising libraries of oligonucleotides or peptides, e.g. in a two-dimensional array format on a planar glass surface.

Preferably, the compounds are immobilised in a solid polymer film to prevent or reduce acid diffusion from irradiated to non-irradiated array elements. Thus, in a further aspect, the present invention provides a polymeric film that comprises one or more of the above compounds. In this embodiment, projection photolithography defines the necessary illumination patterns, activating the compound at defined array elements. The film can then be removed with solvent once irradiation and acid-dependent detritylation is completed and reaction with the nucleosides carried out.

In a further aspect, the present invention provides a method of synthesizing a nucleic acid or peptide array comprising a plurality of elements on a solid support, the method employing a photoactivatable agent which is capable of photolysis to produce a deprotecting agent for removing a protecting group from a nucleic acid molecule or peptide in the array so that it can participate in a chain extension reaction, the method comprising:

(a) providing the photoactivatable agent and a compound capable of neutralising the deprotecting agent at elements in the array;

(b) photolysing the photoactivatable agent at the elements in the array selected for a chain extension reaction;

(c) contacting the deprotected nucleic acid molecule or peptide with nucleosides or amino acids, so that the 5' end of the nucleic acid molecule or peptide reacts with a nucleoside or amino acid; and (d) repeating steps (a) to (c) until the synthesis of the nucleic acid molecule or peptide is complete.

Thus, at elements of the array selected for a chain extension reaction, an excess of the deprotecting agent is generated so that some of the deprotecting agent is not neutralised by the neutralising agent. However, at elements of the array not selected for a chain extension reaction, the production of deprotecting agent by stray light is substantially neutralised by the neutralising agent.

Thus, in elements of the array selected from chain extension, an excess of the deprotecting agent will be produced as compared to the comparatively smaller amount of the neutralising agent. However, in elements of the array which are not selected for chain extension, e.g. elements adjacent a selected element, the production of small amounts of the neutralising agent by stray light directed or reflected to that element will be largely mopped up by the neutralising agent, and will not activate the nucleic acid molecules or peptides in those elements for chain extension, leading to sequence errors.

In a preferred embodiment, the photoactivatable agent is one of the photoactivatable compounds disclosed herein which photolyse to produce halogen substituted carboxylic acid. In situations where the deprotecting agent is an acid, the neutralising agent is conveniently a weak base or a buffer, used in an amount sufficient to neutralise the initial production of the deprotecting compound. Conversely, where the deprotecting agent is a base, the neutralising agent is a weak acid or a buffer.

The method described above is particularly adapted for methods of producing arrays in which projection lithography is used. As disclosed above, stray light can be a problem in such methods as they generally do not employ masks.

Embodiments of the present invention will now be described in more detail by way of example and not limitation with reference to the accompanying figures.

BRIEF DESCRIPTION OF THE FIGURES

FIG. 1 is a graph of the % of oligonucleotide chains without insertions, given by $100\times(1-P)^{3N}$, plotted against contrast ratios on a logarithmic scale from $10^1$ to $10^5$. Data are for N=10, 20 and 30, and exposure for 10 half-times.

FIG. 2 shows analytical reversed phase HPLC data for the products of three synthetic runs.

DETAILED DESCRIPTION

Effect of Stray Light in Maskless Projection Lithography

In one aspect, the present invention provides a solution to a significant but previously unidentified problem in the art to produce high quality arrays by a photodirected method that offers the flexibility and lower costs of maskless projection photolithography, but without the significant losses of array fidelity caused by the stray light associated with DMA projectors or other projection systems such as liquid crystal displays and scanned laser beams modulated either acousto-optically or electro-optically.

This problem arises as the contrast ratio of DMD projectors is about 400, some 250-fold lower than that of metal on glass masks, and necessitates an appraisal of the effects of the higher levels of stray light in photodirected array synthesis. We have not found such an appraisal in the scientific literature, and therefore developed one, as follows.

As already described, photodirected array synthesis (Fodor et al[37], Pease et al[29]) uses photochemistry at scheduled array elements to unblock the oligonucleotide 5'-OH group of the last-coupled nucleotide, thereby allowing reaction with the 3'-phosphoramidite group of the next added nucleotide. Table 2 illustrates the sequence of illuminations, and shows that during the set of 4 synthetic cycles required to extend the array from length n to n+1, each element is exposed to one period of scheduled illumination and three periods of stray light illumination.

The photolysis of photosensitive groups used for 5'-blocking of oligonucleotides is a unimolecular process, and for a given light intensity the kinetics are first order. Removal of >99% of the blocking group requires illumination over many half-times. These half-times can vary with the oligonucleotide base by a factor of up to three[33]. The irradiation exposure is typically set at ten times the slowest base-dependent photolytic half-time (Pease et al[29]).

The time dependent product yield $Y_t$ of a photolytic reaction with first order kinetics is given by the integrated rate equation (equation 1; Williams & Williams[42]) where time t is in units of photolytic half-times:

$$Y_t = 1 - 1/\exp(ln(2)t) \quad (2)$$

If the illumination period is unchanged but the intensity of light is diminished by a factor of 1/R, where R is the contrast ratio, the value $S_t$ for the new extent of photolysis is given by:

$$S_t = 1 - 1/\exp(ln(2)t/R) \quad (3)$$

These integrated rate equations (2) and (3) describe the time course in photodirected array synthesis for the removal by scheduled and stray light respectively of a photosensitive blocking group from the oligonucleotide-5'-OH position. An example of their outcomes is given in Table 3.

As expected, Table 3 shows that the absolute rate of photolysis of a photosensitive blocking group declines with successive half-times of exposure, whereas if the light intensity is reduced by a large factor, the resulting much lower rate of photolysis is effectively constant over the same period.

Calculation of the effects of stray light on the fidelity of array synthesis is simplified by assuming that the photolytic half-time for removal of blocking groups is not base-specific, and that all oligonucleotide chains with unprotected 5'-OH positions are extended by one monomer on contact with nucleoside-3'-phosphoramidites.

At the start of a period of illumination all oligonucleotides are 5'-blocked. The probability that a 5'-protected group will be deprotected during a period of stray light illumination is $S_t$ (equation 3). Assuming that the coupling efficiency with 3'-phosphoramidites is 100%, the value of P for the probability of subsequent chain extension is also equal to $S_t$. The number of chains is very large, so the average number of stray-light induced additions per chain per period of stray-light illumination, for all practical purposes, equals the probability P of their occurrence.

There are 3 periods of stray light illumination per array element per set of four synthetic cycles, and N such sets are required to synthesise an array of N-mers. The average number of stray-light induced additions per chain in the completed array is therefore 3NP. Each unscheduled addition creates a base, and increases the oligonucleotide chain length by one insertion. (Additions at the first and last positions of the chain are included as insertions). If there is no base-specificity for insertions then they will be randomly distributed along the length of the chains.

A suitable statistical model for stray light effects on array synthesis is that of taking a set of shots at a target with a probability P per shot of hitting it. The probability distribution for 0,1,2,3 etc hits per set of shots, or base insertions per oligonucleotide chain (creating lengths of N, N+1, N+2, N+3 etc) is given by the binomial distribution (Bevington[43]). The number of target molecules is very large, so the frequency distribution of insertions is effectively equal to the probability distribution. The most important frequency in the context of array synthesis is for those oligonucleotides with zero insertions and therefore having the designed oligonucleotide sequence. Their frequency can be obtained directly as $(1-P)^{3N}$, where N is the chain length and P $(=S_t)$ is calculated using equation (3) with defined values for the contrast ratio and the exposure period in half-times.

FIG. 1 is a graph of the % of oligonucleotide chains without insertions, given by $100\times(1-p)^{3N}$, plotted against contrast ratios on a logarithmic scale from $10^1$ to $10^5$. Data are for N=10, 20 and 30, and exposure for 10 half-times. The highest value for contrast ratio corresponds to the optical density of 5.0 for chrome-on-quartz masks, where the effect of stray light is negligible. The region of contrast ratio from $10^2$ to $10^3$ includes the values for liquid crystal displays, DMA's, and both acousto-optic and electro-optic modulators. (Modulated and scanned laser beams could in principle be used for generation of array patterns). Stray light effects on array fidelity within this range are considerable, and increase rapidly as the contrast ratio falls.

A more specific example is given in Table 4, which presents calculated values for array fidelity of a 20-mer for contrast ratios from $10^2$ to $10^4$, for exposure of 10 half-times. It illustrates the rapid degradation of array fidelity as the contrast ratio falls below $10^3$. At a contrast ratio of 400:1, typical of the DMD projection devices[40] as used by Singh Gasson et al[38] and LeProust et al[28], 35% of the chains in a 20-mer array would be as designed, whereas 65% would carry one or more base insertions. The binomial distribution in this example for chain lengths N, N+1, N+2, N+3 and N+4 is 35, 37, 19, 6.4 and 1.6% respectively.

It is clear from these calculations (Tables 3 & 4, FIG. 1) that stray light levels associated with DMA projectors would cause significant reductions in the fidelity of oligonucleotide arrays fabricated by a process involving removal of photosensitive 5'-blocking groups. Photodirected oligonucleotide synthesis can also be effected by an indirect method of unblocking oligonucleotide-5'-OH groups. As described in this application, and by others (Beecher et al[31], Gao et al[27], LeProust et al[28]) a photoacid generator is used to achieve photodirected synthesis. The acid, which must be confined by some means to illuminated elements, removes oligonucleotide-5'-dimethoxytrityl groups as in conventional (non-photodirected) oligonucleotide synthesis as described in equation (1).

Two reactions are involved in this indirect method of photodirected synthesis. First, the photogeneration of acid from a precursor, accord to equation (4):

Photoacid generator=Acid+products     (4)

In the simplest case the reaction proceeds via an intramolecular rearrangement of a precursor, where the kinetics are first order and are described by equations (2) and (3). The situation is more complex when the reaction mechanism is not first order, or a second acid generating reaction is added, as with the acid catalysed thermolysis of a non-photosensitive acid precursor (Beecher et al[31]). Irrespective of the method or mechanism, there is no obligation for photolysis and/or thermolysis of the acid generator to proceed to completion: all that is required is for sufficient acid to be generated for the next process, namely, the detritylation of DMT-blocked oligonucleotides according to equation (1).

Detritylation is normally effected with excess acid, and the reaction would therefore behave kinetically as if it were first order. If the reaction does not proceed to completion during any one synthetic cycle, 5'-protected oligonucleotides will remain and fail to be extended by the next exposure to nucleoside-3'-phosphoramidite, reducing the final chain length by 1 per failure (Temsamani et al[44], Fearon et al[45]).

Exposure to acid is therefore arranged to be over many half-times of the detritylation reaction (equation 1), say 10 or more, during which time acid generated by stray light at unscheduled elements will cause a lower but virtually constant rate of detritylation. The situation with indirect photodeprotection is therefore essentially identical to that with the direct route. Consequently, exposure of the array to stray photoacid for multiple detritylation half-times leads to a similar outcome as obtains with stray-light induced 5'-deprotection over multiple photolytic half-times.

The photoacid generated by stray light can be expected to be neutralized by the presence of a sufficient concentration, but not more, of an appropriate buffer, or weak base, to prevent accumulation of stray light generated acid to levels that cause detritylation. The amounts required are low, and can be calculated in the cases where equation (3) applies by using the equation with known values for the photolytic half-time, exposure period, and contrast ratio. For example, with a contrast ratio of 400 and an exposure of 1 photolytic half-time, the amount of acid released by stray light would be 0.17% of the starting concentration of photoacid generator. The latter might typically be 100 mM, so 2-3 mM base or buffer would be several-fold in excess of stray light induced photoacid, without significantly reducing the concentration of acid (50 mM) arising from scheduled illumination for 1 half-time.

It should be noted that the analysis given above for the effects of stray light on oligonucleotide 5'-deprotection is applicable to photolytic deprotection generally when the deprotection is used as part of a synthetic strategy for fabrication of combinatorial arrays. The analysis for the effects of stray light on photoacid generation is also applicable to photobase generation, in which case the effects can be negated by the presence of small amounts of acid or appropriate buffer.

Experimental

1. Synthesis of Photolabile Esters 1.1 Preparation of Precursors

The synthesis of the target photolabile esters required prior preparation of various precursors shown in Scheme 1. 4,5-Dimethoxy-2,6-dinitrobenzaldehyde (1) was prepared by nitration of 4,5-dimethoxy-2-nitrobenzaldehyde following the literature procedure[1]. The latter was made starting from 4-hydroxy-3-methoxybenzaldehyde and improving key steps of the synthetic route described in the literature[2,3]. Rather than following a difficult and low yielding literature procedure[4], 5-chloro-2,6-dinitrobenzaldehyde (2) and 5-chloro-2,4-dinitrobenzaldehyde (3) were prepared by nitration of commercially available 5-chloro-2-nitrobenzaldehyde. 2-Nitrobenzyl alcohol (4) can be purchased from Aldrich but all the substituted benzyl alcohols required as starting materials had to be prepared. Thus 1-(2-Nitrophenyl)-ethanol (5) was made by reduction of 2-nitroacetophenone with sodium borohydride[5]. (2-Nitro-phenyl)-phenyl-methanol (6)[6,7,8], (3-methoxy-phenyl)-(2-nitro-phenyl)-methanol (7), (4-methoxy-phenyl)-(2-nitro-phenyl)-methanol (8)[9,10], (4,5-dimethoxy-2-nitro-phenyl)-(3-methoxy-phenyl)-methanol (9), (4,5-dimethoxy-2-nitro-phenyl)-phenyl-methanol (10)[9,11], (4,5-dimethoxy-2,6-dinitro-phenyl)-phenyl-methanol (11) (5-chloro-2-nitro-phenyl)-phenyl-methanol (12)[12,13] (5-chloro-2,6-dinitro-phenyl)-phenyl-methanol (13) (5-chloro-2,4-dinitro-phenyl)-phenyl-methanol (14) were prepared by condensation of commercially available phenylmagnesium bromide, 3-methoxyphenylmagnesium bromide or 4-methoxyphenylmagnesium bromide with 2-nitrobenzaldehyde, 4,5-dimethoxy-2-nitrobenzaldehyde, 4,5-dimethoxy-2,6-dinitrobenzaldehyde (1), 5-chloro-2-nitrobenzaldehyde, 5-chloro-2,6-dinitrobenzaldehyde (2) and 5-chloro-2,4-dinitrobenzaldehyde (3) in anhydrous tetrahydrofuran at −78° C.[6]. Nucleophilic displacement of the chlorine in commercially available 5-chloro-2-nitrobenzylalcohol, (5-chloro-2-nitro-phenyl)-phenyl-methanol (12)[12,13], 5-chloro-2,6-dinitro-phenyl)-phenyl-methanol (13) or (5-chloro-2,4-dinitro-phenyl)-phenyl-methanol (14), with 2M dimethylamine in methanol, resulted in (5-dimethylamino-2-nitro-phenyl)-methanol (15)[14], (5-dimethylamino-2-nitro-phenyl)-methanol (16), (5-dimethylamino-2-nitro-phenyl)-methanol (17) and (5-dimethylamino-2-nitro-phenyl)-methanol (18), respectively (Scheme 1). Initially the reaction was carried out in a small autoclave and compounds 15 and 16 were obtained in 11-12% yield. The use of a microwave reactor resulted in enhanced rates of the substitution and accordingly compounds 17 and 18 were obtained in virtually quantitative yield.

1.2. Preparation of Esters

Acetic acid and trimethylacetic acid-2-nitrobenzyl esters (20)[15,16] and (21)[17] were prepared by the reaction of appropriate acids with commercially available 2-nitrobenzyl-chloride (19), in the presence of sodium iodide and triethylamine[15] (Scheme 1). Chloroacetic acid, dichloroacetic acid and trichloroacetic acid-2-nitrobenzyl esters (22-24)[18,19] were obtained by esterification of commercially available 2-nitrobenzyl alcohol (4) in the presence of a catalytic amount of sulphuric acid (Scheme 2). Acetylation of compound 5 with the appropriate anhydrides, in the presence of a catalytic amount of sulphuric acid, resulted in the corresponding α-methyl-2-nitrobenzyl esters 25-29 (Scheme 2). In this series, compounds 25[20], 28[21] and 29[17] have been reported previously. (2-Nitro-phenyl)-phenyl-methanol (6)[6,7,8] was acetylated with acetic, chloroacetic, dichloroacetic and trichloroacetic anhydrides (Scheme 2). The best results were obtained when the acetylation was carried out in the presence of pyridine. The corresponding α-phenyl-2-nitrobenzyl esters 30-33 were obtained in 80-90% yield after column chromatography on silicagel. Of the synthesised compounds, in this series only α-phenyl-2-nitrobenzylacetate [acetic-acid (2-nitro-phenyl)-phenyl-methyl ester] (30) has been reported previously[7]. The $^{13}$C-NMR proved particularly diagnostic in the characterisation of these esters, showing clearly resolved signals corresponding to the aromatic carbons at 120-140 ppm, benzylic carbons at 73-77 ppm and acetyl carbons between 25 and 90 ppm depending on the number of chlorine atoms attached. Compounds obtained in this way were more than 95% pure by HPLC. 3-(Methoxy-phenyl)-(2-nitro-phenyl)-methanol (7) was acetylated with chloro and trichloroacetic anhydride in the presence of pyridine. The corresponding α-(3-methoxyphenyl)-2-nitrobenzyl esters (34, 35) were obtained in 80-90% yield after column chromatography on silicagel (Scheme 2). 4-(Methoxy-phenyl)-(2-nitro-phenyl)-methanol (8)[9,10] was acetylated with dichloro or trichloroacetic acid anhydride in the presence of pyridine. Formation of the expected α-(4-methoxyphenyl)-2-nitrobenzyl esters 36 and 37 was observed by TLC but attempts at their purification by column chromatography on silicagel were unsuccessful and the products could only be obtained impure. The major contaminant, however, was isolated and its mass spectrum was consistent with 4'-methoxy-2-nitrosobenzophenone (49), a product of the photolysis of 36 and 37.

These results suggest that α-(4-methoxyphenyl)-2-nitrobenxylacetates are extremely photolabile and special techniques may need to be used for their preparation and handling.

α-Phenyl-4,5-dimethoxy-2-nitrobenzylalcohols 9, 10[9,11] and 11 as well as the 5-dimethylamino-2-nitrobenzylalcohols 15, 16[14], 17 and 18 were acetylated with trichloroacetic anhydride in the presence of pyridine (Scheme 2). The new esters, α-(3-methoxyphenyl)-4,5-dimethoxy-2-nitrobenzyltrichloracetate [trichloroacetic acid (4,5-dimethoxy-2-nitro-phenyl)-(3-methoxy-phenyl)-methyl ester] (38), α-phenyl-4,5-dimethoxy-2-nitrobenzyltrichloroacetate [trichloroacetic acid (4,5-dimethoxy-2-nitro-phenyl)-phenyl-methyl ester] (39), α-phenyl-4,5-dimethoxy-2,6-dinitrobenzyltrichloroacetate [trichloroacetic acid (4,5-dimethoxy-2,6-dinitro-phenyl)-phenyl-methyl ester] (40), 5-dimethylamino-2-nitrobenzyltrichloroacetate [trichloroacetic acid (5-dimethylamino-2-nitro-phenyl)-methyl ester] (41) α-phenyl-5-dimethylamino-2-nitrobenzyltrichloroacetate [trichloroacetic acid (5-dimethylamino-2-nitro-phenyl)-phenyl-methyl ester] (42) and α-phenyl-5-dimethylamino-2,6-dinitrobenzyltrichloroacetate [trichloroacetic acid (5-dimethylamino-2,6-dinitro-phenyl)-phenyl-methyl ester] (43) and α-phenyl-5-dimethylamino-2,4-dinitrobenzyltrichloroacetate [trichloroacetic acid (5-dimethylamino-2,4-dinitro-phenyl)-methyl ester] (44) were isolated in excellent yields.

Their UV spectra showed absorption maxima at 345-323 nm for methoxy substituted compounds 38, 39 and 40 and 395, 398 and 376 nm (with high extinction coefficients) for dimethylamino substituted compounds 41-44 respectively. (See experimental section). All the synthesised compounds were characterised by high resolution mass spectroscopy (HRMS), ultraviolet spectroscopy (UV) and nuclear magnetic resonance spectroscopy (NMR).

1.3. Experimental

Melting points were determined on a Reichert micro hot stage apparatus and are uncorrected. UV spectra were measured in acetonitrile with a Pye-Unicam SP-8-150 UV-vis spectrophotometer. $^1$H NMR spectra were recorded at 250 MHz using a Bruker WH-250 spectrometer with TMS as internal standard. Unless otherwise indicated, DMSO-$d_6$ was used as the solvent. Mass spectra were obtained on a VG ZAB-SE spectrometer with FAB ionisation. Accurate masses were determined with MNOBA+Na as the matrix. HPTLC was run on Merck Kieselgel 60F$_{254}$ analytical plates in the following systems: (A) CH$_2$Cl$_2$/EtOH (49:1), (B) Hexane/EtOAc (9:1), CC) Toluene. Coarse ICN silicagel was used for short column chromatography. 2-Nitrobenzyl alcohol (4), 2-nitrobenzyl chloride (19) 2-nitroacetophenone, phenylmagnesium bromide, 3-methoxyphenylmagnesium bromide, 4-methoxyphenylmagnesium bromide, 2-nitrobenzaldehyde, 5-chloro-2-nitrobenzylalcohol, 5-chloro-2-nitrobenzaldehyde, and 4,5-dimethoxy-2-nitrobenzaldehyde were purchased from Aldrich.

1.4 Preparation of Precursors

1. Preparation of 2,6-dinitrobenzaldehyde (1) 2,6-Dinitrobenzaldehyde (1) was prepared by nitration of 3,4-dimethoxy-2-nitrobenzaldehyde following the literature procedure[1]. 3,4-Dimethoxy-2-nitrobenzaldehyde was prepared starting from 4-hydroxy-3-methoxybenzaldehyde and modifying key steps such as methylation and deacetylation in the published literature procedures[2,3]. The deacetylation was carried out using concentrated aqueous ammonia whereas dimethyl sulphate in acetone was used for the methylation.

2. Preparation of 5-chloro-2,6-dinitrobenzaldehyde (2) 5-Chloro-2-nitrobenzaldehyde (3.25 g, 17.5 mmol) was dissolved in concentrated sulphuric acid (99%, d=1.84, 13 mL) and fuming nitric acid (d-1.501, 2.25 mL) was added dropwise over 5 min at rt. After the addition the mixture was stirred at 55-60° C. for 6 hours. Subsequently, the mixture was cooled to rt and poured onto crushed ice (100 mL). After the ice had melted, dichloromethane (150 mL) was added and the organic layer was washed with water (2×25 mL), 3% aqueous sodium bicarbonate (4×25 mL), brine (30 mL) dried with sodium sulphate and concentrated in vacuo. The residue was purified on a silicagel column eluting with hexane-ethyl acetate (3:1) to give 5-chloro-2,6-dinitrobenzaldehyde as a white solid; yield 0.99 g, 25%, mp 101-102° C. lit [4]102.5-103° C.; $^1$H-NMR δ 8.29 (d, 1H, J=8.92 Hz, H-3), 8.26 (d, 1H, J=8.92 Hz, H-3), 10.2389 (s, 1H, CHO).

3. Preparation of 5-chloro-2,4-dinitrobenzaldehyde (4) 5-Chloro-2-nitrobenzaldehyde (3.25 g, 17.5 mmol) was dissolved in fuming sulphuric acid (30% oleum, d=1.92, 13.5 mL) and fuming nitric acid (d=1.501, 2.5 mL) was added dropwise over 5 min at rt. After the addition the mixture was stirred at 60-65° C. for 6 hours. Subsequently, the mixture was cooled to rt and poured onto crushed ice (100 mL). After the ice had melted, dichloromethane (150 mL) was added and the organic layer was washed with water (2×25 mL), 3% aqueous sodium bicarbonate (4×25 mL), brine (30 mL) dried (sodium sulphate) and concentrated in vacuo. The residue was purified on a silicagel column eluting with hexane-ethyl acetate (17:3) to give 5-chloro-2,4-dinitrobenzaldehyde as a white solid, mp indef; yield 0.82 g, (21%);); observed FAB MS 230.9818, $[C_7H_4\ ClN_2O_5+H]^+$ requires 230.9809; $^1$H-NMR δ 8.22 (s, 1H, H-3), 8.93 (s, 1H, H-4), 10.2647 (s, 1H, CHO)

4. Preparation of (2-nitro-phenyl)-phenyl-methanol (6) (3-methoxy-phenyl)-(2-nitrophenyl)-methanol (7), (4-methoxy-phenyl)-(2-nitro-phenyl)-methanol (8) (4,5-dimethoxy-2-nitro-phenyl)-(3-methoxy-phenyl)-methanol (9), (4,5-dimethoxy-2-nitro-phenyl)-phenyl-methanol (10) (4,5-dimethoxy-2,6-dinitro-phenyl)-phenyl-methanol (11) and (5-chloro-2-nitro-phenyl)-phenyl-methanol (12) (5-chloro-2,6-dinitro-phenyl)-phenyl-methanol (13) (5-chloro-2,4-dinitro-phenyl)-phenyl-methanol (14) (General Procedure)

2-Nitrobenzaldehyde, 4,5-dimethoxy-2-nitro-benzaldehyde, 4,5-dimethoxy-2,6-dinitro-benzaldehyde (1), 5-chloro-2-nitrobenzaldehyde, 5-chloro-2,6-dinitrobenzaldehyde (2), or 5-chloro-2,4-dinitrobenzaldehyde (3), (10 mmol) was dissolved in anhydrous tetrahydrofuran (50 mL) and the solution was cooled to −78° C. Phenylmagnesium bromide, 3-methoxyphenylmagnesium bromide or 4-methoxyphenyl magnesium bromide (1M solution in THF, 10 mL) was added to the stirred solution by syringe during 15 minutes. After 10 minutes at −78° C. the mixture was stirred at −15° C. for 15 minutes. 2% Aqueous hydrochloric acid (100 mL) was added dropwise over 20 minutes followed by dichloromethane (100 mL). Each solution was washed with water (50 mL), 3% aqueous sodium bicarbonate (4×50 mL), water (50 mL), brine (50 mL), dried with anhydrous sodium sulphate and concentrated in vacuo. Each residue was chromatographed on silicagel eluting with dichloromethane/ethanol or dichloromethane to give compounds 6-14.

(2-Nitro-phenyl)-phenyl-methanol (6): yield 81%; Rf (A) 0.42; yellow oil; $^1$H-NMR δ 6.19 (bs, 2H, CH, OH), 7.26 (m, 5H, H-2'-H-6'), 7.42-7.90 (m, 4H, H-3-H-6).

(3-Methoxy-phenyl)-(2-nitrophenyl)-methanol (7): yield 83%; Rf (A) 0.36; yellow oil; $^1$H-NMR δ 3.71 (s, 3H, OCH$_3$), 6.22 (m, 2H, CH, OH), 6.84 (m, 3H, H-2', H-4', H-6'), 7.22 (m, 1H, H-5'), 7.51 (m, 1H, H-4), 7.74 (m, 2H, H-5, H-6), 7.92 (m, 1H, H-3); UV λ$_{max}$ 257 nm ε 4993, λ$_{min}$ 238 nm.

(4-Methoxy-phenyl)-(2-nitro-phenyl)-methanol (8): yield 55%; Rf (A) 0.31; colourless oil; observed FAB MS 294.0755, $[C_{15}H_{13}NO4+Na]^+$ requires 294.0742; $^1$H-NMR δ 3.71 (s, 3H, OCH$_3$), 6.09 (d, 1H, CH, J=4.68 Hz), 6.16 (d, 1H, OH, J=4.68 Hz), 6.85 (m, 2H, H-3', H-5'), 7.14 (m, 2H, H-2', H-6'), 7.51 (m, 1H, H-4), 8.01(m, 3H, H-3, H-5, H-6).

(4,5-Dimethoxy-2-nitro-phenyl)-(3-methoxy-phenyl)-methanol (9): yield 81%; Rf (A) 0.25; reddish oil; δ 3.66 (s, 3H, OCH$_3$), (3.84 (s, 3H, OCH$_3$) 3.87 (s, 3H, OCH$_3$), 6.18 (d, 1H, OH, J=5.46 Hz), 6.29 (m, 2H, CH, H-2'), 6.80 (m, 3H, H-4'-H-6'), 7.40 (s, 1H, H-6), 7.55 (s, 1H, H-3).

(4,5-Dimethoxy-2-nitro-phenyl)-phenyl-methanol (10): yield 69%; Rf (A) 0.34; reddish oil; observed FAB MS 312.0846, $[C_{15}H_{15}NO_5+Na]^+$ requires 312.0848; $^1$H-NMR δ 3.84 (s, 3H, OCH$_3$) 3.88 (s, 3H, OCH$_3$), 6.16 (d, 1H, OH, J=5.03 Hz), 6.30 (d, 1H, CH, J=5.03 Hz) 7.23 (m, 5H, H-2'-H-6'), 7.45 (s, 1H, H-6), 7.56 (s, 1H, H-3); UV λ$_{max}$ 257 nm ε 4993, λ$_{min}$ 238 nm.

(4,5-dimethoxy-2,6-dinitro-phenyl)-phenyl-methanol (11): yield 56%; Rf (A) 0.27; light orange solid; mp indef; observed FAB MS 357.0710, $[C_{15}H_{15}N_2O_7+H]^+$ requires 357.0699; $^1$H-NMR δ 3.90 (s, 3H, OCH$_3$) 3.99 (s, 3H, OCH$_3$), 6.01 (d, 1H, CH, J=3.08 Hz), 6.72 (d, 1H, CH, J=3.08 Hz), 7.23 (m, 5H, H-2'-H-6'), 7.86 (s, 1H, H-3).

(5-Chloro-2-nitro-phenyl)-phenyl-methanol (12): yield 94%; Rf (A) 0.29; light tan oil; $^1$H-NMR δ 6.36 (d, 1H, OH, J=8.01 Hz), 6.73 (d, 1H, CH, J=8.01 Hz), 7.28 (m, 5H, H-2'-H-6'), 7.64 (m, 1H, H-6), 7.82 (m, 1H, H-4) 7.94 (m, 1H, H-3).

(5-chloro-2,6-dinitro-phenyl)-phenyl-methanol (13): yield 83%; Rf (A) 0.32; colourless solid; $^1$H-NMR δ 6.11 (d, 1H, CH, J=4.91 Hz), 6.84 (d, 1H, OH, J=4.91 Hz), 7.30 (m, 5H, H-2'-H-6'), 8.06 (d, 1H, J=8.81 Hz, H-4), 8.20 (d, 1H, J=8.81 Hz, H-3).

(5-chloro-2,4-dinitro-phenyl)-phenyl-methanol (14): yield 48%; Rf (A) 0.40; light yellow oil; $^1$H-NMR δ 6.26 (d, 1H, CH, J=4.80 Hz), 6.60 (d, 1H, OH, J=4.80 Hz), 7.31 (m, 5H, H-2'-H-6'), 8.17 (s, 1H, H-6), 8.73 (s, 1H, H-3).

5. Preparation of (5-dimethylamino-2-nitro-phenyl)-methanol (15) and (5-dimethylamino-2-nitro-phenyl)-phenyl-methanol (16)

(5-Chloro-2-nitro-phenyl)-methanol (0.5 g, 2.67 mmol) or (5-chloro-2-nitro-phenyl)-phenyl-methanol (12) (0.5 g, 1.90 mmol) were treated with 2M solution of dimethylamine in methanol (6 mL) and the solution was heated in a small autoclave at 60-65° C. for 18 hours. The solvent was removed in vacuo and each residue was coevaporated with dichloromethane (3×10 mL) and applied onto a column of silicagel. The column was eluted with dichloromethane/ethanol (49:1) to give compounds 15 and 16.

(5-Dimethylamino-2-nitro-phenyl)-methanol (15): yield 11%; Rf (A) 0.30; yellow oil; $^1$H-NMR δ 3.08 (s, 6H, N (CH$_3$)$_2$), 4.84 (d, 2H, J=4.85 Hz, CH$_2$), 5.42 (t, 1H, J=4.85 Hz, OH), 6.67 (m, 1H, H-6), 7.04 (m, 1H, H-4), 8.04 (d, 1H, J=9.12 Hz, H-3); UV λ$_{max}$ 395 nm ε 17163, λ$_{min}$ 292 nm.

(5-Dimethylamino-2-nitro-phenyl)-phenyl-methanol (16): yield 12%; Rf (A) 0.12; yellow solid, mp 95-97° C.; observed FAB MS 272.1173, $[C_{15}H_{16}N_2O_3+H]^+$ requires 272.1161; $^1$H-NMR δ 3.09 (s, 6H, N(CH$_3$)$_2$), 6.00 (d, 1H, J=5.19 Hz, OH), 6.47 (d, 1H, J=5.19 Hz, CH), 6.70 (m, H-6) 7.21 (m, 6H, H-2'-H-6', H-4), 7.98 (d, 1H, J=9.32 Hz, H-3); UV λ$_{max}$ 398 nm, ε 11435, λ$_{min}$ 322 nm.

6. Preparation of (5-dimethylamino-2,6-dinitro-phenyl)-phenyl-methanol (17) and (5-dimethylamino-2,4-dinitro-phenyl)-methanol (18)

(5-Chloro-2,6-dinitro-phenyl)-phenyl-methanol (13) (0.5 g, 1.90 mmol) or (5-chloro-2,4-dinitro-phenyl)-phenyl-methanol (14) (0.5 g, 2.67 mmol) were treated with 2M solution of dimethylamine in methanol (6 mL) and the solution was heated in a microwave reactor (CEM Focused Microwave™ Synthesis System Model Discover) at 50-55° C. for 15 minutes. The solvent was removed in vacuo and each residue was coevaporated with dichloromethane (2×10 mL) and applied onto a column of silicagel. The column was eluted with dichloromethane/ethanol (49:1) to give compounds 17 and 18.

(5-Dimethylamino-2,6-dinitro-phenyl)-phenyl-methanol (17): yield 94%; Rf (A) 0.22; yellow solid, mp indef; observed FAB MS 340.0895 $[C_{15}H_{15}N_3O_5+Na]^+$ requires 340.0909; $^1$H-NMR δ 2.85 (s, 6H, N(CH$_3$)$_2$), 5.99 (d, 1H, J=5.07 Hz, CH), 6.49 (d, 1H, J=5.07 Hz, OH), 7.24 (m, 6H, H-2'-H-6', H-4), 7.99 (d, 1H, J=9.31 Hz, H-3); UV λ$_{max}$ 387 nm ε 11150.

(5-Dimethylamino-2,4-dinitro-phenyl)-phenyl-methanol (18): yield 91%; Rf (A) 0.35; reddish solid, mp 147-150° C.; observed FAB MS 318.1104, $[C_{15}H_{15}N_3O_5+H]^+$ requires 318.1090; $^1$H-NMR δ 3.04 (s, 6H, N (CH$_3$)$_2$, 6.30 (d, 1H, J=5.17 Hz, CH), 6.44 (d, 1H, J=5.17 Hz, OH), 7.27 (m, 5H, H-2'-H-6'), 7.64 (s, 1H, H-4); 8.52 (s, 1H, H-3); $^{13}$C-NMR δ 42.53 [N(CH$_3$)$_2$], 70.61 (CH), 116.22 (C-6), 126.32 (C-3), 127.86 (C-2', C-4', C-6'), 128.54 (C-3', C-5), 142.84 (C-4), 145.73 (C-2), 148.14 (C-5); UV $\lambda_{max}$ 377 nm $\epsilon$ 16080.

1.5. Preparation of Esters

1. Synthesis of acetic acid 2-nitro-benzyl ester (20) and trimethyl-acetic acid 2-nitro-benzyl ester (21) (General Procedure)

2-Nitrobenzylchloride (19) (1.72 g, 10 mmol) and sodium iodide (100 mg) were suspended in dry ethyl acetate (50 mL). Triethylamine (2.02 g, 2.5 mL) and glacial acetic acid (1.6 g, 2 mL, 20 mmol) or pivaloic acid (2.04 g, 20 mmol) were added to the suspension and the mixture was heated under reflux for 20 h. The solid was filtered off (glass microfibre filter), the filtrate was washed with 1M hydrochloric acid (20 mL), water (2×20 mL), 3% aqueous sodium bicarbonate (2×20 mL), water (20 mL) and brine (20 mL), dried with sodium sulphate and concentrated in vacuo. Each residue was purified by column chromatography on silicagel eluting with dichloromethane/ethanol (500:1) to give products 20 and 21.

Acetic acid 2-nitro-benzyl ester (20): yield 1.58 g (81%); Rf (C) 0.22; yellow solid, mp 53-55° C.; observed FAB MS 196.0606, $[C_9H_9NO_4+H]^+$ requires 196.0610; $^1$H-NMR $\delta$ 2.11 (s, 3H, $CH_3CO$), 5.40 (s, 2H, $CH_2$), 7.59-7.82 (m, 3H, H-4, H-5, H-6), 8.09-8.13 (m, 1H, H-3); UV $\lambda_{max}$ 259 nm $\epsilon$ 4864, $\lambda_{min}$ 232 nm.

Trimethyl-acetic acid 2-nitro-benzyl ester (21): yield 1.72 g (82%); Rf (C) 0.40; yellow oil; observed FAB MS 238.1085 $[C_{12}H_{16}NO_4+H]^+$ requires 238.1079; $^1$H-NMR (CDCl$_3$) $\delta$ 1.16 [s, 9H, $(CH_3)_3C$], 5.39 (s, 2H, $CH_2$), 7.59-7.85 (m, 3H, H-4, H-5, H-6), 8.07-8.11 (m, 1H, H-3); UV $\lambda_{max}$ 259 nm $\epsilon$ 4776, $\lambda_{min}$ 235 nm.

2. Synthesis of chloro-acetic acid 2-nitro-benzyl ester (22), dichloro-acetic acid 2-nitro-benzyl ester (23) and trichloro-acetic acid 2-nitro-benzyl ester (24) (General Procedure)

2-Nitrobenzylalcohol (1.53 g, 10 mmol) and chloroacetic acid (30 mmol), dichloroacetic acid (60 mmol) or trichloroacetic acid (50 mmol) were dissolved in toluene (50 mL) and concentrated sulphuric acid (0.5 mL) was added. Each mixture was heated for 4 hours at 80-90° C. and subsequently chloroform (150 mL) was added. Each solution was washed with water (50 mL), 3% aqueous sodium bicarbonate (4×50 mL), water (50 mL), brine (50 mL), dried with sodium sulphate and concentrated in vacuo. Each residue was chromatographed on silicagel eluting with dichloromethane to give compounds 22-24.

Chloro-acetic acid 2-nitro-benzyl ester (22): yield 72%; Rf (A) 0.86; yellow oil; observed FAB MS 230.0213, $[C_9H_8ClNO_4+H]^+$ requires 230.0220; $^1$H-NMR $\delta$ 4.53 (s, 2H, $ClCH_2CO$), 5.54 (s, 2H, $CH_2$), 7.61-7.84 (m, 3H, H-4, H-5, H-6), 8.12-8.16 (m, 1H, H-3); UV $\lambda_{max}$ 259 nm $\epsilon$ 5120, $\lambda_{min}$ 234 nm.

Dichloro-acetic acid 2-nitro-benzyl ester (23): yield 78%; Rf (A) 0.88; yellow oil; observed FAB MS 263.9821.0213, $[C_9H_7Cl_2NO4+H]^+$ requires 263.983; $^1$H-NMR (CDCl$_3$) $\delta$ 5.72 (s, 2H, $CH_2$), 6.06 (s, 1H, $Cl_2CHCO$), 7.54-7.72 (m, 3H, H-4, H-5, H-6), 8.16-8.19 (m, 1H, H-3); UV $\lambda_{max}$ 259 nm $\epsilon$ 4159, $\lambda_{min}$ 235 nm.

Trichloro-acetic acid 2-nitro-benzyl ester (24); yield 70%; Rf (A) 0.89; yellow oil; observed FAB MS 297.9440 $[C_9H_6Cl_3NO_4+H]^+$ requires 297.9445; $^1$H-NMR (CDCl$_3$) $\delta$, 5.79 (s, 2H, $CH_2$), 7.67-7.89 (m, 3H, H-4, H-5, H-6), 8.17-8.20 (m, 1H, H-3); UV $\lambda_{max}$ 259 nm $\epsilon$ 4975, $\lambda_{min}$ 232 nm.

3. Synthesis of acetic acid 1-(2-nitro-phenyl)-ethyl ester (25), chloro-acetic acid 1-(2-nitro-phenyl)-ethyl ester (26), dichloro-acetic acid 1-(2-nitro-phenyl)-ethyl ester (27), trichloro-acetic acid 1-(2-nitro-phenyl)-ethyl ester (28) and trimethyl-acetic acid 1-(2-nitro-phenyl)-ethyl ester (29) (General Procedure)

1-(2-Nitro-phenyl)-ethanol (5) (1.7 g, 10 mmol) was added dropwise over 10 minutes to a stirred solution of acetic anhydride, chloroacetic anhydride, dichloroacetic anhydride, trichloroacetic anhydride or trimethylacetic anhydride (50 mmol) with the addition of concentrated sulphuric acid (0.5 mL) in toluene (25 mL) at 0° C. After 1 hour at room temperature, each mixture was heated at 80-90° C. for 3 hours and subsequently ethyl acetate (100 mL) was added. Each solution was washed with water (50 mL), 3% aqueous sodium bicarbonate (4×50 mL), water (50 mL) brine (50 mL), dried with sodium sulphate, and concentrated in vacuo. Each residue was chromatographed on silicagel eluting with dichloromethane to give compounds 25-29.

Acetic acid 1-(2-nitro-phenyl)-ethyl ester (25): yield 61%; Rf (A) 0.81; yellow oil; observed FAB MS 210.0775, $[C_{10}H_{11}NO_4+H]^+$ requires 210.0766; $^1$H-NMR $\delta$ 1.56 (d, 3H, J=6.90 Hz, $CH_3$), 2.01 (s, 3H, $CH_3CO$), 6.07 (q, 1H, J=6.90 Hz, CH), 7.53-7.59 (m, 1H, H-4), 7.70-7.77 (m, 2H, H-5, H-6), 7.94-7.97 (m, 1H, H-3); UV $\lambda_{max}$ 256 nm $\epsilon$ 4569 $\lambda_{min}$ 235 nm.

Chloro-acetic acid 1-(2-nitro-phenyl)-ethyl ester (26): yield 34%; Rf (A) 0.73; yellow oil; observed FAB MS 266.0201, $[C_{10}H_{10}ClNO_4+Na]^+$ requires 266.0196; $^1$H-NMR $\delta$ 1.61 (d, 3H, J=6.39 Hz, $CH_3$), 4.43 (s, 1H, $ClCH_2CO$), 6.18 (q, 1H, J=6.39 Hz, CH), 7.62-7.88 (m, 3H, H-4, H-5, H-6), 8.02-8.09 (m, 1H, H-3); UV $\lambda_{max}$ 256 nm $\epsilon$ 5067, $\lambda_{min}$ 234 nm.

Dichloro-acetic acid 1-(2-nitro-phenyl)-ethyl ester (27): yield 64%; Rf (A) 0.83; yellow oil; observed FAB MS 277.9980, $[C_{10}H9Cl_2NO_4+H]^+$ requires 277.9987; $^1$H-NMR $\delta$ 1.67 (d, 3H, J=7.45 Hz, $CH_3$), 6.26 (q, 1H, J=7.45 Hz, CH), 6.93 (s, 1H, $Cl_2CHCO$, 7.62-7.88 (m, 3H, H-4, H-5, H-6), 8.03-8.07 (m, 1H, H-3); UV $\lambda_{max}$ 256 nm $\epsilon$ 4536, $\lambda_{min}$ 235 nm.

Trichloro-acetic acid 1-(2-nitro-phenyl)-ethyl ester (28): yield 64%; Rf (A) 0.91; colourless oil; observed FAB MS 333.9407, $[C_{10}H8Cl_3NO_4+Na]^+$ requires 333.941; $^1$H-NMR $\delta$ 1.73 (d, 3H, J=6.48 Hz, $CH_3$), 6.37 (q, 1H, J=6.48 Hz, CH), 7.62-7.88 (m, 3H, H-4, H-5, H-6), 8.02-8.09 (m, 1H, H-3); UV $\lambda_{max}$ 256 nm $\epsilon$ 4520, $\lambda_{min}$ 234 nm.

Trimethyl-acetic acid 1-(2-nitro-phenyl)-ethyl ester (29): yield 64%; Rf (A) 0.91; colourless oil; observed FAB MS 252.1226 $[C_{13}H_{18}NO_4+H]^+$ requires 252.1236; $^1$H-NMR $\delta$ 1.19 [s, 9H, C $(CH_3)_3$], 1.73 (d, 3H, J=6.52 Hz, $CH_3$), 6.07 (q, 1H, J=6.52 Hz, CH), 7.55-7.59 (m, 1H, H-4), 7.67-7.77 (m, 2H, H-5, H-6), 7.93-7.97 (m, 1H, H-3); UV $\lambda_{max}$ 251 nm $\epsilon$ 6250, $\lambda_{min}$ 237 nm.

4. Synthesis of acetic acid (2-nitro-phenyl)-phenyl-methyl ester (30), chloro-acetic acid (2-nitro-phenyl)-phenyl-methyl ester (31), dichloro-acetic acid (2-nitro-phenyl)-phenyl-methyl ester (32) and trichloro-acetic acid (2-nitro-phenyl)-phenyl-methyl ester (33) (General Procedure)

(2-Nitro-phenyl)-phenyl-methanol (6) (2.29 g, 10 mmol) and acetic anhydride, chloroacetic anhydride, dichloroacetic anhydride or trichloroacetic anhydride (50 mmol) were dissolved in dry dichloromethane (20 mL) and pyridine (0.5 mL) was added by syringe under argon. Each mixture was stirred at room temperature for 8 hours and subsequently ethyl acetate (100 mL) was added. Each solution was washed with water (50 mL), 3% aqueous sodium bicarbonate (4×50 mL), water (50 mL), brine (50 mL), dried with sodium sulphate, and concentrated in vacuo. Each residue was chromatographed on silicagel eluting with dichloromethane to give compounds 30-33.

Acetic acid (2-nitro-phenyl)-phenyl-methyl ester (30): yield 83%; Rf (A) 0.91; yellow oil; observed FAB MS 294.0755, $[C_{15}H_{13}NO_4+Na]^+$ requires 294.0742; $^1$H-NMR δ 2.11 (s, 3H, CH$_3$CO), 7.24 (s, 1H, CH), 7.31-7.40 (m, 5H, H-2'-H-6'), 7.61-7.79 (m, 3H, H-4, H-5, H-6), 8.00-8.03 (m, 1H, H-3); $^{13}$C-NMR δ 20.98 (CH$_3$), 72.01 (CH), 125.02 (C-3), 127.80 (C-4'), 128.78 (C-2', C-6'), 128.95 (C-3', C-5'), 128.98 (C-4), 129.80 (C-6), 134.30 (C-5), 134.56 (C-1), 138.43 (C-1'), 148.29 (C-2), 169.89 (CO); UV $\lambda_{max}$ 257 nm ε 4993, $\lambda_{min}$ 238 nm.

Chloro-acetic acid (2-nitro-phenyl)-phenyl-methyl ester (31): yield 90%; Rf (B) 0.17; yellow oil; $^1$H-NMR δ 4.53 (s, 2H, ClCH$_2$CO), 7.31-7.44 (m, 6H, H-2'-H-6', CH), 7.61-7.85 (m, 3H, H-4, H-5, H-6), 8.04-8.08 (m, 1H, H-3); $^{13}$C-NMR δ 65.17 (CHCl$_2$), 75.14 (CH), 125.22 (C-3), 127.89 (C-4'), 128.91 (C-2', C-6'), 129.00 (C-3', C-5'), 129.03 (C-4), 130.05 (C-6), 133.95 (C-5), 134.51 (C-1), 137.81 (C-1'), 148.10 (C-2), 166.93 (CO); UV $\lambda_{max}$ 257 nm ε 4498, $\lambda_{min}$ 238 nm.

Dichloro-acetic acid (2-nitro-phenyl)-phenyl-methyl ester (32): yield 63%; Rf (B) 0.19; yellow oil; $^1$H-NMR δ 7.03 (s, 1H, Cl$_2$CHCO), 7.36-7.41 (m, 6H, CH, H-2'-H-6'), 7.64-7.70 (m, 2H, H-4, H-6), 7.81-7.85 (m, 1H, H-5), 8.08-8.12 (m, 1H, H-3); $^{13}$C-NMR δ55.26 (CH$_2$Cl), 73.57 (CH), 125.46 (C-3), 127.87 (C-4'), 128.85 (C-2', C-6'), 129.14 (C-3', C-5'), 129.27(C-4), 130.41 (C-6), 133.16 (C-5), 134.55 (C-1), 137.09 (C-1'), 148.10 (C-2), 163.65 (CO); UV $\lambda_{max}$ 257 nm ε 4156, $\lambda_{min}$ 241 nm.

Trichloro-acetic acid (2-nitro-phenyl)-phenyl-methyl ester (33): yield 69%; Rf (B) 0.21; yellow oil; $^1$H-NMR δ 7.44 (bs, 5H, arom), 7.51 (s, 1H, CH) 7.62-7.70 (m, 2H, H-4, H-6,), 7.86 (m, 1H, H-5), 8.12 (m, 1H, H-3); $^{13}$C-NMR δ 77.46 (CH), 89.49 (CCl$_3$), 125.63 (C-3), 127.88 (C-4'), 128.96 (C-2', C-6'), 129.23 (C-3', C-5'), 129.50 (C-4), 130.69 (C-6), 132.59 (C-5), 134.76 (C-1), 136.53 (C-1'), 148.18 (C-2), 160.33 (CO); UV $\lambda_{max}$ 257 nm ε 4442, $\lambda_{min}$ 238 nm.

5. Synthesis of chloro-acetic acid (3-methoxy-phenyl)-(2-nitro-phenyl)-methyl ester(34) and trichloro-acetic acid (3-methoxy-phenyl)-(2-nitro-phenyl)-methyl ester (35) (General Procedure)

(3-Methoxy-phenyl)-(2-nitro-phenyl)-methanol (7) (2.59 g, 10 mmol) and chloroacetic anhydride or trichloroacetic anhydride (50 mmol) were dissolved in dry dichloromethane (20 mL) and pyridine (0.5 mL) was added by syringe under argon. Each mixture was stirred at room temperature for 8 hours and subsequently ethyl acetate (100 mL) was added. Each solution was washed with water (50 mL), 3% aqueous sodium bicarbonate (4×50 mL), water (50 mL), brine (50 mL), dried with sodium sulphate and concentrated in vacuo. Each residue was chromatographed on silicagel eluting with dichloromethane to give compounds 34 and 35.

Chloro-acetic acid (3-methoxy-phenyl)-(2-nitro-phenyl)-methyl ester (34): yield 91%; yellow oil; Rf (A), 0.67; observed FAB MS 335.0573, $[C_{16}H_{14}ClNO_5+Na]^+$ requires 335.0561; $^1$H-NMR δ 3.76 (s, 3H, OCH$_3$), 4.27 (s, 1H, ClCH$_2$CO), 6.91-6.97 (m, 3H, CH, H-2'-H-4'), 7.30-7.35 (m, 2H, H-5', H-6'), 7.66-7.82 (m, 2H, H-4, H-6), 7.85-7.91 (m, 1H, H-5), 8.05-8.09 (m, 1H, H-3); UV $\lambda_{max}$ 266 nm ε 4792, $\lambda_{min}$ 243 nm.

Trichloro-acetic acid (3-methoxy-phenyl)-(2-nitro-phenyl)-methyl ester (35): yield 93%; yellow oil; Rf (A) 0.75; observed FAB MS 404.62 $[C_{16}H_{12}Cl_3NO_5+Na]^+$ requires 404.63; $^1$H-NMR δ 3.73 (s, 3H, OCH$_3$), 6.97-7.09 (m, 3H, CH, H-2'-H-4'), 7.36 (m, 1H, H-6'), 7.53-7.57 (m, 1H, H-5'), 7.69-7.73 (m, 2H, H-4, H-6), 7.80-7.84 (m, 1H,H-5), 8.11-8.15 (m, 1H, H-3); UV $\lambda_{max}$ 265 nm ε 5091, $\lambda_{min}$ 244 nm.

6. Synthesis of dichloro-acetic acid (4-methoxy-phenyl)-(2-nitro-phenyl)-methyl ester (36) and trichloro-acetic acid (4-methoxy-phenyl)-(2-nitro-phenyl)-methyl ester (37) (General Procedure)

(4-Methoxy-phenyl)-(2-nitro-phenyl)-methanol (8) (2.59 g, 10 mmol) and dichloroacetic anhydride or trichloroacetic anhydride (50 mmol) were dissolved in dry dichloromethane (20 mL) and pyridine (0.5 mL) was added by syringe under argon. Each mixture was stirred at room temperature for 8 hours and subsequently ethyl acetate (100 mL) was added. Each solution was washed with water (50 mL), 3% aqueous sodium bicarbonate (4×50 mL), water (50 mL), brine (50 mL), dried with sodium sulphate and concentrated in vacuo. Each residue was chromatographed on silicagel eluting with dichloromethane to give compounds 36 and 37.

Dichloro-acetic acid (4-methoxy-phenyl)-(2-nitro-phenyl)-methyl ester (36) (obtained impure due to instability): yield 81%; yellow oil rapidly decomposing on storage; Rf (A) 0.71; $^1$H-NMR δ 3.77 (s, 3H, OCH$_3$) 6.96-7.05 (m, 2H, H-3', H-5'), 7.09 (s, 1H, Cl$_2$CHCO), 7.36-7.41 (m, 3H, CH, H-2', H-6'), 7.66-7.73 (m, 2H, H-4, H-6), 7.85-7.91 (m, 1H, H-5), 8.09-8.14 (m, 1H, H-3).

Trichloro-acetic acid (4-methoxy-phenyl)-(2-nitro-phenyl)-methyl ester (37) (obtained impure due to instability): yield 93%; yellow oil rapidly decomposing on storage; Rf (A) 0.78; $^1$H-NMR δ 3.75 (s, 3H, OCH$_3$) 6.96-7.11 (m, 2H, H-3', H-5'), 7.28-7.34 (m, 2H, H-2', H-6'), 7.44 (s, 1H, CH), 7.64-8.30 (m, 4H, H-3-H-6); UV $\lambda_{max}$ 267 nm ε 11504 nm, $\lambda_{min}$ 246 nm.

7. Synthesis of trichloro-acetic acid (4,5-dimethoxy-2-nitrophenyl)-(3-methoxyphenyl)-methyl ester (38), trichloro-acetic acid (4,5-dimethoxy-2-nitrophenyl)-phenyl-methyl ester (39)) and trichloro-acetic acid (4, 5-dimethoxy-2,6-dinitrophenyl)-phenyl-methyl ester (40) (General Procedure)

(4,5-Dimethoxy-2-nitrophenyl)-(3-methoxyphenyl)-methanol (7) (3.19 g, 10 mmol) or (4,5-dimethoxy-2-nitrophenyl)-phenyl-methanol (10) (2.89 g, 10 mmol) or (4,5-dimethoxy-2,6-dinitrophenyl)-phenyl-methanol (11) (2.89 g, 10 mmol) and trichloroacetic anhydride (50 mmol) were dissolved in dry dichloromethane (20 mL) and pyridine (0.5 mL) was added by syringe under argon. Each mixture was stirred at room temperature for 6 hours and subsequently ethyl acetate (100 mL) was added. Each solution was washed with water (50 mL), 3% aqueous sodium bicarbonate (4×50 mL), water (50 mL), brine (50 mL), dried with sodium sulphate and concentrated in vacuo. Each residue was chromatographed on silicagel eluting with dichloromethane to give compounds 38-40.

Trichloro-acetic acid (4,5-dimethoxy-2-nitrophenyl)-(3-methoxyphenyl)-methyl ester (38); yield 81%; yellow oil; Rf (A) 0.87; $^1$H-NMR δ 3.73 (s, 3H, OCH$_3$), 3.82 (s, 3H, OCH$_3$) 3.89 (s, 3H, OCH$_3$) 6.92-7.03 (m, 4H, CH, H-2', H-4', H-6'), 7.30-7.37(m, 1H, H-5'), 7.52 (s, IH, H-6), 7.73 (s, 1H, H-3); UV $\lambda_{max}$ 344 nm ε 5064, $\lambda_{min}$ 246 nm.

Trichloro-acetic acid (4,5-dimethoxy-2-nitrophenyl)-phenyl-methyl ester (39); yield 67%; yellow solid; Rf (A) 0.74; observed FAB MS 432.9871, $[C_{17}H_{14}Cl_3NO_6]^+$ requires 432.9887; $^1$H-NMR δ 3.84 (s, 3H, OCH$_3$), 3.89 (s, 3H, OCH$_3$), 7.09 (s, H, CH), 7.42 (m, 5H, H-2'-H-6'), 7.55 (s, 1H, m, H-6), 7.74 (s, 1H, H-3); UV $\lambda_{max}$ 345 nm ε 5250, $\lambda_{min}$ 272 nm.

Trichloro-acetic acid (4,5-dimethoxy-2,6-dinitrophenyl)-phenyl-methyl ester (40); yield 79%; yellow solid, mp 105-106° C.; Rf (A) 0.79; observed FAB MS 611.8800,

[C$_{17}$H$_{13}$Cl$_3$N$_2$O$_8$+Cs]$^+$ requires 611.8792; $^1$H-NMR δ 3.92 (s, 3H, OCH$_3$), 4.04 (s, 3H, OCH$_3$), 7.10 (s, H, CH), 7.28-7.42 (m, 6H, H-2'-H-6', CH), 8.03 (s, 1H, H-5); $^{13}$C-NMR δ 57.88 (OCH$_3$), 62.79 (OCH$_3$), 74.88 (CH), 89.16 (CCl$_3$), 112.11 (C-4), 115.01(C-1), 126.56 (C-3', C-5'), 128.77 (C-2', C-6'), 129.07 (C-4'), 135.40 (C-1'), 144.27 (C-2), 144.73 (C-6), 145.36 (C-4), 153.89 (C-5), 160.95 (CO); UV λ$_{max}$ 323 nm ε 4110.

8. Synthesis of trichloro-acetic acid 5-dimethylamino-2-nitro-benzyl ester (41), trichloro-acetic acid (5-dimethylamino-2-nitro-phenyl)-phenyl-methyl ester (42), trichloro-acetic acid (5-dimethylamino-2,6-dinitro-phenyl)-phenyl-methyl ester (43) and trichloro-acetic acid (5-dimethylamino-2,4-dinitro-phenyl)-phenyl-methyl ester (44) (General Procedure)

(5-Dimethylamino-2-nitro-phenyl)-methanol (15) (0.217 g, 1 mmol), (5-dimethylamino-2-nitro-phenyl)-phenyl-methanol (16) (0.272 g, 1 mmol), (5-dimethylamino-2,6-dinitro-phenyl)-phenyl-methanol (17) (0.317 g, 1 mmol) or (5-dimethylamino-2-nitro-phenyl)-phenyl-methanol (18) (0.317 g, 1 mmol) and trichloroacetic anhydride (5 mmol) were dissolved in dry dichloromethane (5 mL) and pyridine (0.1 mL) was added by syringe under argon. Each mixture was stirred at room temperature for 6 hours and subsequently ethyl acetate (50 mL) was added. Each solution was washed with water (5 mL), 3% aqueous sodium bicarbonate (4×5 mL), water (5 mL), brine (5 mL), dried with sodium sulphate and concentrated in vacuo. Each residue was chromatographed on silicagel eluting with dichloromethane to give compounds 41-44.

Trichloro-acetic acid (5-dimethylamino-2-nitro-phenyl)-phenyl-methyl ester (41): yield 78%; yellow froth; Rf (A) 0.85; $^1$H-NMR δ 3.08 [s, 6H, N(CH$_3$)$_2$], 6.84 (m, 2H, H-4, H-6) 7.39 (m, 5H, H-2'-H-6'), 7.72 (s, 1H, CH), 8.13 (d, 1H, J=9.40 Hz, H-3); UV λ$_{max}$ 398 nm ε 18344, λ$_{min}$ 295 nm.

Trichloro-acetic acid 5-dimethylamino-2-nitro-benzyl ester (42): yield 44%; yellow foam; Rf (A), 0.88; observed FAB MS 472.8842, [C$_{11}$H$_{11}$Cl$_3$N$_2$O$_4$Cs]$^+$ requires 472.8839; $^1$H-NMR δ 3.08 [s, 6H, N(CH$_3$)$_2$], 5.78 (s, 2H, CH$_2$), 6.82 (m, 2H, H-4, H-6), 8.04 (d, 1H, J=9.20 Hz, H-3); UV λ$_{max}$ 395 nm ε 16680, λ$_{min}$ 292 nm.

Trichloro-acetic acid (5-dimethylamino-2,6-dinitro-phenyl)-phenyl-methyl ester (43): yield 80%; yellow solid, mp 129-130° C.; Rf (A) 0.85; observed FAB MS 462.0040, [C17H$_{14}$Cl$_3$N$_3$O$_6$+H]$^+$ requires 462.0026; $^1$H-NMR δ 3.08 [s, 6H, N(CH$_3$)$_2$], 6.84 (m, 2H, H-4, H-6) 7.39 (m, 5H, H-2'-H-6'), 7.72 (s, 1H, CH), 8.13 (d, 1H, J=9.40 Hz, H-3); $^{13}$C-NMR δ 41.72 [N(CH$_3$)$_2$], 76.05 (CH), 89.24 (CCl$_3$), 119.14 (C-4), 126.59 (C-3', C-5'), 128.54 (C-2', C-3, C-6'), 128.84 (C-4'), 136.64 (C-1'), 137.68 (C-1), 138.33 (C-2), 148.30 (C-5), 161.27 (CO); UV λ$_{max}$ 376 nm ε 11000.

Trichloro-acetic acid (5-dimethylamino-2,4-dinitro-phenyl)-phenyl-methyl ester (44): yield 73%; yellow solid, mp 91-92° C.; Rf (A) 0.68; observed FAB MS 593.8980, [C17H$_{14}$Cl$_3$N$_3$O$_6$+Cs]$^+$ requires 593.9003; $^1$H-NMR δ 3.01 [s, 6H, N(CH$_3$)$_2$], 7.23 (s, 1H,CH); 7.42 (m, 5H, H-2'-H-6'), 8.67 (s, 1H, H-3); $^{13}$C-NMR δ 42.61 [N(CH$_3$)$_2$], 77.99 (CH), 89.51 (CCl$_3$), 115.57 (C-6), 127.21(C-3), 128.73 (C-3', C-5'), 129.17 (C-2', C-6'), 129.74 (C-4'), 134.06 (C-1), 134.43 C-1'), 135.71 (C-2), 138.17 (C-4), 148.06 (C-5), 160.15 (CO); UV λ$_{max}$ 376 nm ε 16000.

2. Irradiation of Photolabile Esters 2.1 Results

Compounds 20-28, 5% solutions in acetonitrile, were irradiated in a semi-micro photochemical reactor provided by Photochemical Reactors Ltd. The photochemistry of 2-nitrobenzyl esters is reported to be unchanged within the range 254-314 nm[17] (Scheme 3). Irradiation was carried out at 254 nm, the predominant wavelength of the low pressure Hg arc provided with the reactor. Despite the fact that a weak four-watt lamp was used as the source of UV light, a limited photolysis (c.5%) in the 2-nitrobenzyl series and a very clear photolysis (20-30%) in the α-methyl-2-nitrobenzyl series was observed. The photolysis was monitored by HPLC. 2-Nitrosobenzaldehyde (45) was the only UV detectable photoproduct formed in the 2-nitrobenzyl series and similarly 2-nitrosoacetophenone (46) was the sole product of photolysis in the α-methyl-2-nitrobenzyl series (Scheme 3). The detector used in the HPLC apparatus cannot detect the putative carboxylic acids generated during the photoreaction. The estimated degree of photoconversion for esters 20-24 was around 5% whereas for esters 25-28 was 20-30%. α-Phenyl-2-nitrobenzyl esters 30-33, 5% solutions in acetonitrile, were also irradiated at 254 nm (Scheme 3). The response was much more pronounced than in the α-methyl series; each of the esters gave the same, expected product of photolysis, 2-nitrosobenzophenone (47), in 40-50% yield, and its structure was confirmed by HRMS and NMR. The photoreactions were very selective with only small amounts of side products being detected.

Irradiation of esters 30-33 at 350 nm in the same photoreactor, using a weak four watt UV lamp, 1, 6", black phosphor coated with peak emission at 350 nm, also resulted in a good response. This response may be attributed to the high concentration of the esters causing complete light absorption at 350 nm as well as 254 nm. Again, each of the irradiated esters gave the same and expected products of photolysis, 2-nitrosobenzophenone (47), and the corresponding carboxylic acid, in 30-40% yield. The photoreactions were even more selective than those carried out at 254 nm with no side products being detected.

The analogous α-methyl-2-nitrobenzylesters (25-28) described above, having less light absorption at 350 nm than compounds 30-33, did not respond to irradiation at 350 nm.

A more powerful 100 W high pressure mercury arc lamp was initially used for the irradiation of α-phenyl-2-nitrobenzyltrichloroacetate (33) and α-(3-methoxyphenyl)-2-nitrobenzyl-trichloroacetate (35) at 365 nm (Scheme 3). The rate of photoconversion was monitored by HPLC, TLC and UV. Depending on the concentration of solution (0.002-2% in acetonitrile) and the length of light path used (1-10 mm) the rate of photoconversion varied between 20% and 90% for a 5 min irradiation. The products of photolysis, 2-nitrosobenzophenone (47) and 3'-methoxy-2-nitrosobenzophenone (48), were isolated by HPLC and showed by mass spectroscopy to be the same as those isolated previously during irradiations at 254 and 350 nm in the photoreactor described above. Secondary photoproducts were not observed under the conditions of relatively weak irradiation used in the photoreactor (4 W lamp), but were observed when the 100 W high pressure Hg arc lamp was used for extended time.

Irradiation of a 2 mm film of 0.2% solution α-3-methoxyphenyl-2-nitrobenzyltrichloroacetate[trichloro acetic acid (3-methoxy-phenyl)-(2-nitro-phenyl)-methyl ester] (35) with the high pressure mercury arc lamp, in a flat bottom vial, gave a nearly quantitative photoconversion to compound 48 after 5 minutes.

Irradiation of 0.2% solutions of α-(3-methoxyphenyl)-4,5-dimethoxy-2-nitrobenzyltrichloroacetate (38) and α-phenyl-4,5-dimethoxy-2-nitrobenzyltrichloroacetate (39) in acetonitrile resulted in nearly quantitative conversions into the expected photoproducts, 4,5-dimethoxy-3'-methoxy-2- nitrosobenzophenone (50) and 4,5-dimethoxy-2-nitrosobenzophenone (51), respectively, after less than 4 minutes. Irradiations at lower concentrations, monitored by UV, resulted in even faster photoreactions. When a 0.004% solution of α-phenyl-4,5-dimethoxy-2-nitrobenzyltrichloroacetate (39) was irradiated, there was a quantitative conversion into the photoproduct after 30 seconds. The two esters appeared to have a similar rate of photoconversion but the photolysis of α-phenyl-4,5-dimethoxy-2-nitrobenzyltrichloroacetate (39), quantum yield φ~0.14, was cleaner with less amount of polar secondary photoproducts. These properties, coupled with the reduced inner filter effect and absorption maximum at 345 nm, make compound 39 a prime candidate for use in the microarray format.

Photolysis of 5-dimethylamino-2-nitrobenzyltrichloroacetate (41) and α-phenyl-5-dimethylamino-2-nitrobenzyltrichloroacetate (42) appeared to be of particular promise. They have absorption maxima at 395 and 398 nm, respectively, with molar extinction coefficients of around 17000 $M.cm^{-1}$. The photolysis of compound 41, with no substitution at the α-position, was slower than that of the esters having an α-substitution[16,17]. Thus irradiation at 0.2% concentration, at 365 nm, gave the expected photoproduct, 5-dimethylamino-2-nitrosobenzaldehyde (53), in 30% yield after 16 min. In addition, the amount of accompanying secondary photoproducts, around 10%, was the highest among the esters evaluated so far. On the other hand, irradiations at lower concentrations indicated that the inner filter effect was diminishing as the photolysis proceeded. This was not the case with any esters tested by us before. Preliminary illuminations of compound 41 with blue light, λ>395 nm, at 0.002% concentration, carried out with the high pressure mercury arc lamp equipped with appropriate filters, gave about 12% photoconversion after 16 min. This result indicates that the development of photolabile esters whose activation would require considerably less expensive sources of visible light is feasible.

It was expected that the photolysis of compound 42 having an α-phenyl substitution[16,17], would be faster than that of compound 41. However, its rate of photoconversion was similar to that of compound 41. Furthermore, HPLC analysis indicated the formation of several primary or secondary photoproducts.

Irradiations of the synthesised esters with the high pressure mercury arc lamp and He/Cd laser showed that α-phenyl-4,5-dimethoxy-2-nitrobenzyltrichloroacetate (39) gave the highest rate of desired photoconversion with virtually no secondary photoproducts. This, coupled with the absorption maximum at 345 nm, make this compound a good candidate for the use as a photoacid generator in the microarray format.

Compounds 33 and 39 that emerged as the best photoacid generators were assessed for their suitability to effect indirect photodetritylation. This involved their irradiations in the presence of 5'-O-dimethoxytrityl protected nucleosides and oligonucleotides in indirect photodetritylations on solid support and in solution as well as irradiations in the presence of 5'-O-dimethoxytrityl protected nucleosides attached to commercially available controlled porosity glass (CPG).

These experiments demonstrated that complete photodetritylation is possible even if a weak source of light was employed but irradiation times required were between 70 and 140 minutes. Thus, >99% yield detritylation was achieved when 1% solution of ester 39 in dichloromethane[22] was irradiated for 70 minutes in the presence of commercially available 5'1'-O-DMTr-T-CPG. Successful, part manual, part automated syntheses of DMTrTT, DMTrTTT, DMTrTTTT, DMTrTTTTT and DMTrATATA were also carried out. α-Phenyl-2-nitrobenzyltrichloroacetate (33), was employed in the manual photodetritylation step performed in the photoreactor, whereas the condensation, oxidation and capping were carried out on the synthesiser using appropriate automated, computer controlled protocols.

We also determined whether the detritylation could be achieved at lower concentrations of trichloroacetic acid. The usual trichloroacetic acid concentration for detritylation is 2-3% (w/v), corresponding to c. 120-180 mM. The photoacid precursor used, α-phenyl-4,5-dimethoxy-2-nitrobenzyltrichloroacetate (39), has a millimolar extinction coefficient of 3.0 $mM.cm^{-1}$ at 365 nm, the most suitable excitation wavelength available from a high pressure Mercury arc lamp. The absorption at 365 nm, of a 1 mm depth of a 120-180 mM ester solution is therefore 36-54. Such solutions are effectively opaque to light at 365 nm and obviously more dilute solutions of the ester were required.

A series of experiments involved the measurements of detritylation kinetics from CPG and from Expedite membranes using dilute trichloroacetic acid and photogenerated trichloroacetic acid in solution. It was established that the rates of photoconversion were considerably higher whereas inner filter effects were considerably lower for 10-20 mM solutions of the ester in dichloromethane. 10 mM Trichloroacetic acid in dichloromethane effected complete detritylation of 5'-O-dimethoxytrityl protected nucleosides after 300 seconds. The findings of this study were used to develop protocols for the automated synthesis on a DNA synthesiser.

2.2 Measurements of Quantum Yields for Photolysis of Esters 2.2.1 Methods

Quantum yields of modest accuracy are useful for ranking the value of the individual members of a set 2-nitrbenzyl esters as photoacid generators. We devised a relatively simple method that follows the time dependent course of changes in the UV-Visible absorption spectrum of an ester solution during photolysis. Wavelength values for absorption maxima and minima, and extinction coefficients, are given above in the Experimental Section. We assumed that the photolytic reaction has first order kinetics. The half-time for the reaction ($t_{half}$), defined operationally as the time for taken for the spectral changes to proceed to 50% completion, is related to the first order rate constant k by the equation $k=0.693/t_{half} \sec^{-1}$.

The initial rate of photolysis at the onset of irradiation is the product of k and the amount of ester in the illuminated cuvette. The rate of light absorption at the onset of irradiation is the product of the incident light power and the fractional absorption of light by the solution. The later value is equal to $1-10_{-A}$, where A is the absorption of the ester solution at the excitation wavelength prior to illumination. The quantum yield Φ is defined as the ratio of the rate of photolysis, expressed as molecules per second, to the rate of light absorption expressed as photons per second.

If the photolysis rate is expressed as μmoles/s and the light absorption rate as mJ/sec, then the quantum yield can be conveniently calculated as Quantum yield=(photolysis rate)/(light absorption rate)×(a wavelength dependent constant). This constant incorporates the appropriate molecular and optical conversion factors and has a value of $3.38 \times 10^2$ at 365 nm, and $2.96 \times 10^2$ at 405 nm. The half-life itself can be obtained either from the slope of a plot of log (fraction of ester unphotolysed) versus time, or more rapidly but less accurately by inspection of a set of absorption spectra recorded during photolysis and including both zero and full photolysis.

2.2.2 Results

The Table summarizes our results using the above methods as applied to several esters. All excitations were at 365 nm. Solutions of esters were either at low (50-150 μM) or substantially higher (5.4-5-6 mM concentration. In the later cases all incident light is absorbed, and spectroscopic changes were followed by dilution of intermittent samples into 3.0 ml of solvent (dichloromethane). The ranges given for the quantum yield are those for 2-3 separate determinations.

TABLE

Quantum yields for photolysis of several esters at 365 nm

| Ester | Φ |
|---|---|
| α-Phenyl-5-dimethylamino-2-nitrobenzyltrichloracetate (41) | <0.01 |
| α-Phenyl-5-dimethylamino-2,4-dinitrobenzyltrichloracetate (44) | 0.003-0.005 |
| α-Phenyl-5-dimethylamino-2,6-dinitrobenzyltrichloracetate (43) | 0.04-0.08 |
| α-Phenyl-4,5-dimethoxy-2-nitrobenzyltrichloracetate (39) | 0.12-0.15 |
| α-Phenyl-4,5-dimethoxy-2,6-dinitrobenzyltrichloracetate (40) | 0.43-0.46 |

2.3 Experimental 5 2.3.1 Irradiations of Photolabile Esters in the Photoreactor

Compounds 20-44 were irradiated in a semi-micro photochemical reactor provided by Photochemical Reactors Ltd. Irradiations were carried out using a four watt UV 10 lamp with peak emission at 254 nm or 350 nm. The progress of photolysis was monitored by HPLC and TLC. Reverse phase HPLC was performed using a Waters chromatography system with a variable wavelength detector set at 254 nm and 280 nm. Columns, Waters Delta Pak 5 μ C18-300A, were used for analytical and preparative scales. The mobile phases were (A) 0.05 M aq. [Et$_3$NH]$^+$[CH$_3$COO]$^-$(B) MeCN. Gradient elution; 5%(B)-90% (B) over 30 minutes.

Irradiation of α-phenyl-2-nitrobenzyltrichloroacetate [trichloro-acetic acid (2-nitro-phenyl)-phenyl-methyl ester] (33)

α-Phenyl-2-nitrobenzyltrichloroacetate (33), 5% (w/v) solution in acetonitrile (3.5 mL), in a 1 cm quartz cuvette, was irradiated in the photoreactor at 350 nm for 70 minutes. The irradiated solution was analysed by HPLC showing the presence of the starting material, retention time R$_t$=18.33 min, and the photoproduct, R$_t$=15.15 min. The estimated degree of photoconversion, peak areas, was 15%. Preparative HPLC resulted in two fractions, fraction 1, retention time 15.15 min fraction 2, retention time 18.33 min. Each fraction was analysed by MS; the photoproduct, 2-nitrosobenzophenone (47), was found in fraction 1; (M+H) 212.1.

Similarly, esters 22-44 were irradiated in the photoreactor at 254 nm and 350 nm giving a varying degree of photoconversion. Each photoproduct (45-56) was isolated by preparative HPLC, estimated yield in brackets, and its identity was confirmed by mass spectroscopy; (M+H) values given in brackets.

Acetic acid 2-nitro-benzyl ester (20): R$_t$13.67 min

Trimethyl-acetic acid 2-nitro-benzyl ester (21): R$_t$ not determined

Chloro-acetic acid 2-nitro-benzyl ester (22): R$_t$ 15.44 min

Dichloro-acetic acid 2-nitro-benzyl ester (23): R$_t$ not determined.

Trichloro-acetic acid 2-nitro-benzyl ester (24): R$_t$ not determined.

Acetic acid 1-(2-nitro-phenyl)-ethyl ester (25): R$_t$ 14.57 min.

Chloro-acetic acid 1-(2-nitro-phenyl)-ethyl ester (26): R$_t$ 15.44 min.

Dichloro-acetic acid 1-(2-nitro-phenyl)-ethyl ester (27): R$_t$ 16.40 min.

Trichloro-acetic acid 1-(2-nitro-phenyl)-ethyl ester (28): R$_t$ 17.24 min.

Trimethyl-acetic acid 1-(2-nitro-phenyl)-ethyl ester (29): R$_t$ not determined.

Acetic acid (2-nitro-phenyl)-phenyl-methyl ester (30): R$_t$ 15.88 min.

Chloro-acetic acid (2-nitro-phenyl)-phenyl-methyl ester (31): R$_t$ 16.48 min.

Dichloro-acetic acid (2-nitro-phenyl)-phenyl-methyl ester (32): R$_t$ 17.20 min.

Trichloro-acetic acid (2-nitro-phenyl)-phenyl-methyl ester (33): R$_t$ 18.33 min.

Chloro-acetic acid (3-methoxy-phenyl)-(2-nitro-phenyl)-methyl ester(34): R$_t$ not determined.

Trichloro-acetic acid (3-methoxy-phenyl)-(2-nitro-phenyl)-methyl ester (35):R$_t$ 16.77 min.

Dichloro-acetic acid (4-methoxy-phenyl)-(2-nitro-phenyl)-methyl ester (36): R$_t$ 16.22 min.

Trichloro-acetic acid (4-methoxy-phenyl)-(2-nitro-phenyl)-methyl ester (37): R$_t$ not determined.

2-Nitrosobenzaldehyde (45)[23]: R$_t$ 12.08 min (M+H) 135.1 (5-7% at 254 nm).

2-Nitrosoacetophenone (46)[24]: R$_t$ 12.25 min; (M+H) 150.1 (20-30% at 254 nm).

2-Nitrosobenzophenone (47)[25]: R$_t$ 15.15 min; (M+H) 212.1 (40-50% at 254 nm; 30-40% at 350 nm); observed FAB MS 212.0701, [C$_{13}$H$_{10}$NO$_2$+H]$^+$ requires 212.0712; $^{13}$C-NMR δ 120.26 (C-3), 127.87 (C-3', C-5'), 128.78 (C-2', C-6'), 129.15 (C-1) 129.34 (C-4), 129.41 (C-4'), 131.59 (C-5), 136.86 (C-1'), 163.91 (C-2), 195.94 (CO).

3'-Methoxy-2-nitrosobenzophenone (48): R$_t$14.11 min; (M+H) 242.1 (30-40% at 350 nm) observed FAB MS 242.0828, [C$_{15}$H$_{14}$NO$_4$+H]$^+$ requires 242.0817.

4'-Methoxy-2-nitrosobenzophenone (49): R$_t$ 14.22 min; (M+H) 242.1 50%.

Preparative scale irradiation of α-phenyl-4,5-dimethoxy-2-nitrobenzyltrichloroacetate[trichloro-acetic acid (4,5-dimethoxy-2-nitro-phenyl)-phenyl-methyl ester] (39), α-phenyl-4,5-dimethoxy -2,6-dinitrobenzyltrichloroacetate [trichloro-acetic acid (4,5-dimethoxy-2,6-dinitro-phenyl)-phenyl-methyl ester] (40) and α-phenyl-5-dimethylamino-2,6-dinitrobenzyltrichloroacetate [trichloro-acetic acid (5-dimethylamino-2,6-dinitro-phenyl)-phenyl-methyl ester] (43)

Esters 39 and 40, 2% solution in dichloromethane (3.5 mL), and ester 43, 0.25% solution in dichloromethane (3.5 mL), were irradiated in the photoreactor at 350 nm for 200 minutes. The degree of photoconversion could be conveniently monitored by TLC. Each solution was concentrated to a half of its volume and applied onto a column of silicagel (4 g, Coarse silicagel). The column was eluted with CH$_2$Cl$_2$, appropriate fractions were combined and the solvent was removed in vacuo. The residue was dissolved in water/ethanol (1:1) (2 mL) and freeze-dried to give the photoproduct.

4,5-Dimethoxy-2-nitrosobenzophenone (51); yield 62%; Rf (CH$_2$Cl$_2$,) 0.58; green-yellow froth, observed FAB MS 272.0920, [C$_{15}$H$_{14}$NO$_4$+H]$^+$ requires 272.0923; $^1$H-NMR δ 3.89 (s, 3H, OCH$_3$), 4.00 (s, 3H, OCH$_3$), 6.74 (s, 1H, H-3), 7.44 (s, 1H, H-6), 7.54 (m, 2H, H-3', H-5'), 7.63 (m, 1H, H-4') 7.75 (m, 2H, H-2', H-6'); $^{13}$C-NMR δ 56.37(OCH$_3$), 57.38 (OCH$_3$), 95.32(C-3), 110.39(C-6), 129.15 (C-3', C-5'), 129.64 (C-2', C-6'), 134.13 (C-4') 137.18 (C-1), 138.06 (C-1'), 150.36 (C-5), 156.82 (C-4), 160.78 (C-2), 195.99 (CO); UV λ$_{max}$ 385 nm ε 8762.

4,5-Dimethoxy-6-nitro-2-nitrosobenzophenone (52); yield 69%; Rf (CH$_2$Cl$_2$,) 0.64; yellow froth, observed FAB MS 317.0778, [C$_{15}$H$_{13}$N$_2$O$_6$+H]$^+$ requires 317.0774; $^1$H-NMR δ 3.89 (s, 3H, OCH$_3$), 4.00 (s, 3H, OCH$_3$), 6.74 (s, 1H, H-3), 7.44 (s, 1H, H-6), 7.54 (m, 2H, H-3', H-5'), 7.63 (m, 1H, H-4'), 7.75 (m, 2H, H-2', H-6'); $^{13}$C-NMR δ 57.80 (OCH$_3$), 63.10 (OCH$_3$), 101.31 (C-3), 126.38 (C-1), 126.55 (C-4'), 129.39 (C-3', C-5'), 129.48 (C-2', C-6'), 134.92 (C-4'), 137.39 (C-1'), 148.21 (C-5), 154.65 (C-4), 158.36 (C-2), 191.85 (CO); UV λ$_{max}$ 372 nm ε 4433.

5-Dimethylamino-6-nitro-2-nitrosobenzophenone (55); yield 47%; Rf (CH$_2$Cl$_2$,) 0.66; yellow solid, mp indef; $^1$H-NMR δ 2.90 [s, 6H, N(CH$_3$)$_2$], 6.28 (d, 1H, J=8.72 Hz, H-4), 7.48 (m, 5H, H-2'-H-6'), 8.25 (d, 1H, J=8.72 Hz, H-3); $^{13}$C-NMR δ 43.50 [N(CH$_3$)$_2$], 98.96 (C-4), 107.78 (C-3), 126.96 (C-1), 128.04 (C-3', C-5'), 129.29 (C-4'), 129.95 (C-2', C-6'), 130.40 (C-1'), 132.77 (C-6), 144.97 (C-5), 151.70 (C-2), 166.62 (CO); UV λ$_{max}$ 447 nm ε 20550.

Irradiation of α-phenyl-4,5-dimethoxy-2-nitrobenzyl-trichloroacetate [trichloro-acetic acid (4,5-dimethoxy-2-nitro-phenyl)-phenyl-methyl ester] (39) in the presence of 5'-O-dimethoxytritylthymidine bound to controlled porosity glass (5'-O-DMTr-T-CPG).

Commercially available 5'-O-DMTr-T-CPG (50 mg with a loading of 35 μmole/g) was treated with 2% solution of ester 31 in dichloromethane (3.5 mL). The mixture was irradiated at 350 nm for 70 minutes. The solution turned orange. The solid was filtered off, washed thoroughly with dichloromethane and dried in a desiccator over P$_2$O$_5$. A weighed sample of the solid was treated with a measured amount of 3% trichloroacetic acid in dichloromethane and subsequently absorption at 494 nm was measured indicating that the detritylation occurred in>90% yield.

2.3.2 Irradiations of Photolabile Esters using 100 W High Pressure Mercury Arc Lamp A more powerful and intense source of ultraviolet irradiation was provided by a 100 W high pressure Hg arc lamp (Osram HBO 100 W/2)in a Photon Technology International ("PTI") f/4.5 ellipsoidal reflector unit model A-1010B, and powered with an LPS-220B supply (also from PTI). Cooling was by water circulation with a closed cycle cooling box from On-Line Instruments Systems ("OLIS"). The reflected beam from the lamp was passed through a liquid heat filter (Oriel Instruments Model 6123) that provides an 80 mm optical path length through water. The beam was then passed through the following Schott filters, each 3 mm thick: KG1 (further heat removal), WG320 (removal of UV light below 320 nm) and UG1 (transmission of UV-light between 310 and 390 nm). The final output consisted therefore of predominantly the 365 nm Hg arc line, with a much smaller contribution from the 334 nm line. The output was then focussed with a suitable lens or lenses to the face of a stoppered quartz cuvette, volume 4.0 ml and path length 1 cm.The contents of the cuvette were stirred at c.5 Hz with an 8×3 mm magnetic stirring bar, driven through a local drive unit and remote control unit (Variomag Model MINI, H+P Labortechnik GmBH).

The light power falling on the cuvette was measured with a Melles Griot Broadband 2 W Power/Energy Meter model 13 PEM001. The detector, which has a 10 mm diameter thermopile, was positioned to collect light passing through the cuvette position, and the power measured in the of the cuvette's absence was equated with the incident power in its presence. The output of the Hg arc measured at the cuvette position fell with lamp age, from about 120 mW for a new lamp to about 30 mW for a used lamp about to fail. Attenuation of these incident powers was achieved when required with changes of beam focussing and/or the introduction of a metal mask with a hole immediately prior to the cuvette. A mechanical shutter was used to achieve complete attenuation.

All exposures of solutions to UV irradiation were carried out at room temperature in the range 18-22° C. Absorption spectra of the irradiated solutions were obtained by transferring the cuvette and its contents to a Beckman Model DU-7 spectrophotometer and measuring against a solvent blank. Alternatively, when the peak absorption of the contents was high (>1.5), a sample was taken from the cuvette with a micro syringe and diluted into a final volume of 3.0 ml of solvent in another cuvette on which the measurements were made.

The progress of photolysis was monitored by HPLC and TLC. Reverse phase HPLC was performed using a Waters chromatography system with a variable wavelength detector set at 254 nm and 280 nm. Columns, Waters Delta Pak 5μ C18-300A, were used for analytical and preparative scales. Unless otherwise indicated the mobile phases were (A) 0.05 M aq. [Et$_3$NH]$^+$[CH$_3$COO]$^-$ (B) MeCN. Gradient elution 5% B-90% B over 30 minutes.

Compounds 33, 35, 38-44 were irradiated in a 1 mm quartz cuvette using a 100 W high-pressure mercury arc lamp.

Irradiation of α-phenyl-4,5-dimethoxy-2-nitrobenzyl-trichloroacetate [trichloro-acetic acid (2-nitro-phenyl)-phenyl-methyl ester] (39)

α-Phenyl-4,5-dimethoxy-2-nitrobenzyltrichloroacetate (39), 0.2% (w/v) solution in acetonitrile in a 1 mm quartz cuvette, was irradiated at 365 nm. Samples were taken at regular, 30 sec, intervals and analysed by HPLC showing the presence of the starting material, retention time R$_t$=16.68 min, and the photoproduct, R$_t$=13.45. The estimated degree of photoconversion after 240 seconds was 90%. Preparative HPLC resulted in two fractions, fraction 1, retention time 16.68 min and fraction 2, retention time 13.45 min. Each fraction was analysed by MS; the photoproduct, 4,5-dimethoxy-2-nitrosobenzophenone (51), was found in fraction 1; (M+H) 272.1.

Similarly, esters 33, 35, 38, 40, 41,42,43 and 44 were irradiated in a 1 mm quartz cuvette at 365 nm giving a varying degree of photoconversion. Each photoproduct (47, 48, 50-56) was isolated by preparative HPLC, estimated yield in brackets, and its identity was confirmed by mass spectroscopy; (M+H) values given where appropriate. Trichloro-acetic acid (2-nitro-phenyl)-phenyl-methyl ester (33): R$_t$ 18.33 min.

Trichloro-acetic acid (3-methoxy-phenyl)-(2-nitro-phenyl)-methyl ester (35): R$_t$ 16.77 min.

Trichloro-acetic acid (4,5-dimethoxy-2-nitrophenyl)-(3-methoxyphenyl)-methyl ester (38): R$_t$ 17.02 min.

Trichloro-acetic acid (4,5-dimethoxy-2-nitrophenyl)-phenyl-methyl ester (39): R$_t$ 16.63 min.

Trichloro-acetic acid (4,5-dimethoxy-2,6-dinitrophenyl)-phenyl-methyl ester (40): $R_t$ not determined.

Trichloro-acetic acid (5-dimethylamino-2-nitro-phenyl)-phenyl-methyl ester (42): $R_t$ 17.62 min.

Trichloro-acetic acid (5-dimethylamino-2,6-dinitro-phenyl)-phenyl-methyl ester (43): $R_t$ 14.42 min (A) 0.05M aq. $[Et_3NH]^+[HCO_3]^-$ (B) MeCN. Gradient elution over 30 minutes.

Trichloro-acetic acid (5-dimethylamino-2,4-dinitro-phenyl)-phenyl-methyl ester (44): $R_t$ not determined 2-Nitrosobenzophenone (47): $R_t$ 15.15 min; (M+H) 212.1 (90%, 300 seconds).

3'-Methoxy-2-nitrosobenzophenone (48): $R_t$ 14.11 min; (M+H) 242.1 (80%, 240 seconds, TLC).

3'-Methoxy-4,5-dimethoxy-2-nitrosobenzophenone (50): $R_t$ 14.25 min; (M+H) 302.0 (23%, 120 seconds).

4,5-Dimethoxy-2-nitrosobenzophenone (51): $R_t$ 13.45 min; (M+H) 272.0 (90%, 240 seconds).

4,5-Dimethoxy-6-nitro-2-nitrosobenzophenone (52): $R_t$ 13.45 min; (M+H) 317.1.

5-Dimethylamino-2-nitrosobenzaldehyde (53)[26]: $R_t$ 15.83 min; (M+H) 179.2 (30%, 16 min)

5-Dimethylamino-2-nitrosobenzophenone (54): $R_t$ 16.87 min; (M+H) 255.1.

5-Dimethylamino-2-nitro-6-nitrosobenzophenone (55): $R_t$ 14.77 min (A); (M+H) 300.3 0.05M aq. $[Et_3NH]^+[HCO_3]^-$ (B) MeCN. Gradient elution over 30 minutes. (70%, 45 minutes TLC).

5-Dimethylamino-4-nitro-2-nitrosobenzophenone (56): $R_t$ not determined; (M+H) 300.3.

Irradiation of α-phenyl-4,5-dimethoxy-2-nitrobenzyl-trichloroacetate [trichloro-acetic acid (4,5-dimethoxy-2-nitro-phenyl)-phenyl-methyl ester] (39) in the presence of 5'-O-dimethoxytritylthymidine bound to controlled porosity glass (5'-O-DMTr-T-CPG)

Commercially available 5'-O-DMTr-T-CPG (35 µmol/g) (5 mg) was treated with 1% (w/v) solution of ester 39 in dichloromethane (4.0 mL). The mixture was irradiated at 365 nm for 5 minutes. The solution turned orange. The solid was filtered off, washed thoroughly with dichloromethane and dried in a desiccator over $P_2O_5$. A weighed sample of the solid was treated with a measured amount of 3% trichloro-acetic acid in dichloromethane. Subsequently, absorption at 494 nm was measured indicating that the detritylation occurred in>99% yield.

Conclusion: Photogenerated trichloroacetic acid in dichloromethane at 10-16 mM gives>99% detritylation of DMT-T.

Preparative scale irradiation of α-phenyl-5-dimethylamino-2,6-dinitrobenzyltrichloroacetate [trichloro-acetic acid (5-dimethylamino-2,6-dinitro-phenyl)-phenyl-methyl ester] (43) and α-phenyl-5-dimethylamino-2,4-dinitrobenzyltrichloroacetate [trichloro-acetic acid (5-dimethylamino-2,4-dinitro-phenyl)-phenyl-methyl ester] (44)

Esters 43 and 44, 0.25% solution in dichloromethane (3.5 mL), were irradiated in the photoreactor at 350 nm for 200 minutes. The degree of photoconversion could be conveniently monitored by TLC. Each solution was concentrated to a half of its volume and applied onto a column of silicagel (4 g, coarse silicagel). The column was eluted with $CH_2Cl_2$, appropriate fractions were combined and the solvent was removed in vacuo. The residue was dissolved in water/ethanol (1:1) (2 mL) and freeze-dried to give the photoproduct.

5-Dimethylamino-2-nitroso-6-nitrobenzophenone (55); yield 58%; spectroscopic data were consistent with those quoted above for the same compound.

5-Dimethylamino-2-nitroso-4-nitrobenzophenone (56); yield 27%; Rf ($CH_2Cl_2$,) 0.45; yellowsolid; $[M+H]^+$300.2; $^1$H-NMR δ 3.11 [s, 6H, $N(CH_3)_2$], 7.18 (s, H-6, 7.25-7.76 (m, 5H, H-2'-H-6'), 8.03 (s, 1H, H-3).

2.3.3 Titration of Acid Production from the Photolysis of α-phenyl-4,5-dimethoxy-2-nitrobenzyl trichloroacetate [trichloro-acetic acid (4,5-dimethoxy-2-nitro-phenyl)-phenyl-methyl ester] (39) using tetrabromophenol-blue as indicator Acid production from photolysis of 4,5-dimethoxy-2-nitrobenzyltrichloroacetate (39) was measured by titration with alkali and a visual indicator (tetrabromophenol blue, pK c.3.5. Aldrich).

Irradiation was performed using a 100 W water-cooled high pressure Hg arc, Schott glass filters to isolate a broad band from 330 to 380 nm (KG12 heat filter, WG320 blocking below 320 nm, and UG1, all 3 mm thick.). Glass cuvettes, 1 cm light path, volume 4.0 mL, were used as reaction vessels. Starting concentrations of the ester in 3.1 mL of acetonitrile ranged from 19 to $222 \times 10^{-6}$M.

Illumination time was 2 min for ester concentrations less than $148 \times 10^{-6}$M, otherwise 3 min. Samples were stirred during illumination by hand with a plastic stirrer rod. After illumination, tetrabromophenol blue, sodium salt, was added to a concentration of $22 \times 10^{-6}$ M. The blue colour of the indicator disappeared except for the controls lacking either ester or irradiation. Standardised solutions of sodium methoxide were then added to the cuvettes, with stirring, until the indicator became blue/green.

Results: The amount of acid required to restore the blue/green colour of indicator added to irradiated cuvettes was proportional to the starting concentration of ester. The slope of the plot was 0.92, close to the theoretical value of 1.0.

Conclusion: The results clearly identify the formation of acid in amounts close to the expected amount from ester photolysis.

SUMMARY

Photolytic acid production from α-phenyl-4,5-dimethoxy-2-nitrobenzyl-trichloroacetate (39) was measured by titration of UV-irradiated solutions with sodium methoxide solutions, using tetrabromophenol blue (pK 3.5) as indicator. Irradiation times, illumination geometry and internal filter effect made for non-optimal conditions, and possibly led to underestimate of the degree of photolysis. Nevertheless, the amount of acid produced was proportional to the amount of ester photolysed over a range of initial ester concentrations. The molar ratio of acid produced to ester photolysed was 0.92, in reasonable agreement with the theoretical value of 1.0.

2.3.4 Photodetritylation using α-phenyl-5-dimethylamino-2,6-dinitrobenzyltrichloracetate (43)

Experimental Design

The experiment takes advantage of the strong visible absorption band of the dimethoxytrityl cation (DMTr$^+$) in acid ($\lambda_{max}$=498 nm, $E_{mM}$=80). However, the presence of a large excess of the photoproduct(s) of 43 interferes with absorption measurement of DMTr$^+$ in the 450-520 nm region. An indirect approach was therefore taken in which the amount of DMTr$^-$ remaining on cpg after exposure to a solution of illuminated 43 was measured after separation of the cpg particles by centrifugation and, following a wash and further centrifugation to remove residual contamination by supernatant, addition of 3% trichloroacetic acid to the particles. The added trichloroacetic acid rapidly detritylates residual DMTr-T-cpg, releasing DMTr⁺. The absorbance of the suspension of cpg in acid at 498 nm therefore accurately reflects the amount of DMTr that was attached to the cpg particles after exposure to a solution of 43 with or without exposure to UV light.

2.3.4.1. Experimental Procedure and Results

Dichloromethane was used for all solutions and washes. DMTrT-cpg particles(accurately measured to be within ±3% of 5 mg dry weight) were added to 3.0 ml of dichloromethane containing 2.54 mg of 43 per mL in a 4.0 ml quartz cuvette of path length 1 cm. A small magnetic stirring bar was added, and the cuvette was sealed with its stopper. The cuvette was placed in the output beam of the Hg ars lamp, as described above under "Instruments" and exposed to UV light power of 108 mW for 20 minutes. Absorption spectra from 300-600 nm of 100-fold diluted samples of the cuvette contents before and after irradiation confirmed that extensive photolysis had occurred in that time, as evidenced by the fall in absorption of the main peak of the ester at 376 nm and the emergence of the new peak of the major photoproduct at 450 nm.

The cpg particles of each sample (i.e. irradiated test and non-irradiated control) were separated from their supernatants by transferring them to glass centrifuge tubes with 35 ml of dichloromethane and briefly centrifuged. The supernatant was removed. After a further wash the particles were taken up in 5.0 ml of 3% (w/v) trichloroacetic acid. The control particles gave an intense orange colour whereas the test particles gave no detectable colour. Spectrophotometric measurement showed the expected peak at 498 nm (absorption value>3.0), whereas the test sample showed no increase over a solvent baseline at an absorption detection limit of 0.005.

Conclusion: these data demonstrate that DMTt-T-cpg present during the photolysis of 43 became at least 99.9% detritylated.

3. Automated Photodirected Synthesis of Oligonucleotides 3.1. Automated Photodirected Oligonucleotide Synthesis on the DNA Synthesiser using a High Pressure Mercury Arc Lamp with a Flexible Light Guide A high-pressure mercury arc lamp with an UV conducting liquid light guide, suitable for attaching to the automated oligonucleotide synthesiser, was used to irradiate solutions of the esters being passed through modified flow columns housing controlled porosity glass (CPG). The automated photodirected syntheses of a control pentamer, DMTrTTTTT, demonstrated that the best results were obtained when 300 pulses, around 4.5 mL, of a 1% (22 mM)(solution of α-phenyl-4,5-dimethoxy-2-nitrobenzyltrichloroacetate (39) in dichloromethane were passed over 1800 seconds through the irradiated modified flow column, housing 0.5 µmole of CPG, during each detritylation step. This ensured sufficient steady state concentrations of photogenerated trichloroacetic acid (2-4 mM) as well as adequate continued flow during photolysis on the synthesiser to avoid the effects of unstirred and unilluminated volumes. As estimated by MS and HPLC the overall yield was at least 81.8% which corresponded to 95.1% stepwise yield. It was found that a similar yield was obtained when the pentamer was made using the conventional synthetic protocol with 3% trichloroacetic acid in dichloromethane. The same protocol was employed in the synthesis of a variety of sequences which included DMTrTTTTT, DMTrTATAT DMTrTGTGT, DMTrTTTTTTTTTT, DMTrATATATATAT, DMTrCTCTCTCTCT and DMTr TGCATTGCAT and the yield of desired products was essentially the same irrespective of whether trichloroacetic acid was added directly at 183 mM concentration or generated photochemically from 22 mM precursor.

For example, the estimated stepwise yield for synthesis of DMTrTTTTTTTTTT, in our hands was 97.8% for the photochemical method and 98% for the conventional method. The yield for a TT coupling using the conventional method is generally considered to be in the region of 98-99%, so we have little if any room for improvement. Coupling efficiencies involving purine nucleosides, particularly guanosine, are usually lower. Overall yields, using either conventional or photodirected methods, depend strongly on the performance of a DNA synthesiser used. This is reflected in the total and stepwise yields obtained by us and presented in Table 5.

These results clearly demonstrate that detritylation performed using photogenerated trichloroacetic acid is as effective as that achieved by conventional 183 mM trichloroacetic acid in dichloromethane. The nitroso photoproduct does not appear to block the newly exposed 5'-OH group of the oligonucleotides. To our knowledge no other group has achieved equality of yield between photodirected and conventional syntheses. Two groups, at Affymetrix and Houston, using photoacid generators available from the semiconductor industry, fell several % Short[27,28,29].

The use of α-phenyl-4,5-dimethoxy-2,6-dinitrobenzyltrichloroacetate (40) instead of α-phenyl-4,5-dimethoxy-2-nitrobenzyltrichloroacetate (39), also resulted in equality of yield between photodirected and conventional syntheses. The high quantum yield and increased rate of photolysis of compound 40, highlighted earlier, enabled not only the use of its more dilute solutions but also considerable shortening of synthetic cycles. The automated photodirected syntheses of a control pentamer, DMTrTTTTT, demonstrated that the best results were obtained when 150 pulses, around 2.2 mL, of a 0.5% (11 mM) solution of compound 40 in dichloromethane were passed over 900 seconds through the irradiated modified flow column, housing 0.5 µmole of CPG, during each detritylation step. This improved and shortened protocol was employed in the synthesis of a variety of sequences which included DMTrTTTTT, DMTrTATAT DMTrTGTGT, DMTrTTTTTTTTTT, DMTrATATATATAT, DMTrCTCTCTCTCT, DMTrGTGTGTGTGT and DMTrTGCATTGCAT and the results are presented in Table 8.

Like its counterpart 51 described above, 4,5-dimethoxy-6-nitro-2-nitrosobenzophenone (52), the photoproduct formed as a result of the irradiation of α-phenyl-4,5-dimethoxy-2,6-dinitrobenzyltrichloroacetate (40) does not appear to block the newly exposed 5'-OH group of the oligonucleotides.

3.2. Experimental

We used a Millipore Expedite DNA synthesiser with modified polypropylene flow columns and provision of a shuttered UV source (365 nm line from a 100 W high pressure Hg arc, from Linos) to illuminate the column through a flexible light guide and suitable optical filters and lenses using either α-phenyl-2-nitrobenzyltrichloroacetate (39), or α-phenyl-2,6-dinitrobenzyltrichloroacetate (40), in place of the conventional direct addition of trichloroacetic acid. Three hundred pulses, (4.5 mL), of a 1% (w/v) (22 mM) solution of α-phenyl-4,5-dimethoxy-2-nitrobenzyltrichloroacetate (39) in dichloromethane were passed over 1800 seconds through the irradiated modified flow column, housing 0.5 µmole of 5'-O-DMTr-T-CPG (controlled porosity glass), during each detritylation step whereas the same step performed using α-phenyl-4,5-dimethoxy-2,6-dinitrobenzyltrichloroacetate (40) required one hundred fifty pulses, (2.2 mL), of its 0.5% (w/v) (11 mM) solution in dichloromethane passed over 900 seconds through the irradiated modified flow column, housing 0.5 µmole of 5'-O-DMTr-T-CPG (controlled porosity glass). Otherwise conditions were as usual, with conventional computer controlled DNA 1 micromole protocols for capping, oxidation, coupling and washing.

Each photodirected synthesis was followed by a control, conventional synthesis in which 3% trichloroacetic acid in dichloromethane was used instead of the photoacid generator. After the completion of each synthesis the solid support was treated with concentrated ammonium hydroxide (2 mL) for 18 h at room temperature. The solid was filtered off and concentrated in vacuo on the Speedvac rotary concentrator.

Each residue was analysed by reverse phase HPLC. The reverse phase HPLC was performed using a Waters chromatography system with a variable wavelength detector set at 254 nm and 280 nm. Columns, Waters Delta Pak 5µ C18-300A, were used for analytical and preparative scales. Unless otherwise indicated the mobile phases were A) 0.05M aq. [Et$_3$NH]$^+$ [CH$_3$COO]$^-$ B) MeCN. Gradient elution; 5% B -60% B over 30 minutes.

Each analytical HPLC was followed by a preparative HPLC; collected fractions were freeze-dried and analysed by electro-spray mass spectroscopy. Yields, retention times and mass spectra of synthesised trityl-on oligonucleotides using ester 39 are presented in Tables 5 and 6. Subsequent detritylation of purified sequences obtained using ester 39 was carried out with 3% aqueous acetic acid over 12-15 min at room temperature (22-25°). The same reverse phase columns were used for analytical and preparative HPLC of the detritylated sequences. The mobile phases were A) 0.05M aq. [Et$_3$NH]$^+$[HCO3]$^-$B) MeCN. Gradient elution; 5% B-60% B over 30 minutes. Retention times and mass spectra of synthesised trityl-off oligonucleotides are presented in Table 7. Yields, retention times and mass spectra of synthesised trityl-on oligonucleotides using ester 40 are presented in Tables 8 and 9.

TABLE 1

Actions in the photodirected synthesis of an oligonucleotide array. Steps 1 to 4 constitute a synthetic cycle. They must occur 4 times to extend the array by 1 base, and 4N times to make an array of N-mers. A, C, G & T refer to the nucleoside bases.

| Stage | Action |
| --- | --- |
| Start | Glass surface with attached linkers. The terminal —OH group is blocked with a photosensitive group, as are the 5'-OH groups of subsequently added nucleoside phoshoramidites. |
| Step 1 | Deblock the protected —OH at selected elements by patterned illumination |
| Step 2 | Couple 5'-O-protected nucleoside phosphoramidite A to free —OH groups |
| Step 3 | Cap non-reacted —OH groups with acetic anhydride |
| Step 4 | Oxidise the trivalent phosphite bond to pentavalent phosphate |
| Step 5 | Return to Step 1 and repeat in turn for monomers C, G & T. |
| Step 6 | Continue by repeating steps 1 to 5 for N-1 times to make an array of N-mers |
| Finish | Deprotect exocyclic N-groups |

TABLE 2

Illumination sequence during extension of an oligonucleotide array from length n to n + 1.

| Synthetic cycle no. | Added base | Illumination at elements for A, C, G or T- | | | |
| --- | --- | --- | --- | --- | --- |
| | | A | C | G | T |
| 1 | A | Scheduled | Stray | Stray | Stray |
| 2 | C | Stray | Scheduled | Stray | Stray |
| 3 | T | Stray | Stray | Scheduled | Stray |
| 4 | G | Stray | Stray | Stray | Scheduled |

TABLE 3

Exposure time and photolysis by scheduled and stray light. The exposure time is in units of the half-time for photolysis by scheduled light. The calculations use equations (1) and (2) for scheduled light and stray light respectively, and a contrast ratio of 400:1.

| Exposure time (half-times) | 0 | 0.0625 | 0.125 | 0.25 | 0.5 | 1 | 2 | 4 | 8 | 16 |
| --- | --- | --- | --- | --- | --- | --- | --- | --- | --- | --- |
| Scheduled photolysis (%) | 0 | 4.24 | 8.30 | 15.9 | 29.3 | 50.0 | 75.0 | 93.8 | 99.6 | 100 |
| Stray light photolysis (%) | 0 | 0.011 | 0.022 | 0.043 | 0.086 | 0.17 | 0.35 | 0.69 | 1.4 | 2.7 |

TABLE 4

Calculated effect of stray light at different contrast ratios on the % of sequences identical to the designed sequences by photodirected synthesis of a 20-mer array using direct photodeprotection for 10 half-lives.

| Contrast ratio | $1 \times 10^4$ | $4 \times 10^3$ | $2 \times 10^3$ | $1 \times 10^3$ | $4 \times 10^2$ | $2 \times 10^2$ | $1 \times 10^2$ |
| --- | --- | --- | --- | --- | --- | --- | --- |
| % of correct sequences | 96 | 90 | 81 | 66 | 35 | 13 | 1.6 |

TABLE 5

Yields of Oligonucleotides Obtained by Conventional or Photodirected Synthesis; Ester 39

| Oligonucleotide (DMTr-) | Synthetic Yields of Oligonucleotides (%) | | | | Ratio of stepwise yields: Photodirected/Conventional |
|---|---|---|---|---|---|
| | Photodirected | | Conventional | | |
| | Overall | Stepwise | Overall | Stepwise | |
| -(T)$_5$ | 81.8 | 95.1 | 75.9 | 93.3 | 1.019 |
| -TATAT | 65.2 | 89.9 | 64.9 | 89.8 | 1.001 |
| -TGTGT | 59.3 | 87.8 | 56.1 | 86.5 | 1.016 |
| -(T)$_{10}$ | 82.0 | 97.8 | 83.7 | 98.0 | 0.997 |
| -(TA)$_5$ | 51.7 | 92.1 | 51.9 | 93.0 | 0.990 |
| -(TC)$_5$ | 59.1 | 94.3 | 58.3 | 94.2 | 1.001 |
| -(TGCAT)$_2$ | 60.1 | 94.5 | 65.0 | 95.3 | 0.992 |

TABLE 6

Retention Times and Mass Spectra of Synthesised Oligonucleotides; Ester 39

| Oligonucleotide | Retention Time (min). Photodirected | Molecular Ion Observed. Photodirected | Retention Time (min). Conventional | Molecular Ion Observed. Conventional |
|---|---|---|---|---|
| DMTrTTTTT | 13.35 | 1759.6 [M − H]$^-$ | 13.32 | 1759.6 |
| DMTrTATAT | 13.10 | 1777.3 [M − H]$^-$ | 13.07 | 1777.3 |
| DMTrTGTGT* | 12.75 | 1809.3 [M − H]$^-$ | 12.70 | 1809.3 |
| DMTrTTTTTTTTTT | 12.92 | 1639.6 [M − 2H]$^{2-}$ | 12.85 | 1639.6 |
| DMTrTATATATATA | 12.25 | 1662.4 [M − 2H]$^{2-}$ | 12.22 | 1662.4 |
| DMTrTCTCTCTCTC | 12.30 | 1602.1 [M − 2H]$^{2-}$ | 12.27 | 1602.1 |
| DMTrTGCATTGCAT* | 12.25 | 1658.6 [M − 2H]$^{2-}$ | 12.27 | 1658.5 |

*0.05 M triethylammonium bicarbonate buffer/acetonitrile

TABLE 7

Retention Times and Mass Spectra of Synthesised Oligonucleotides; Ester 39

| Oligonucleotide (5'-3') | Retention Time (min). Photodirected | Molecular Ion Observed. Photodirected | Retention Time (min). Conventional | Molecular Ion Observed Conventional |
|---|---|---|---|---|
| TTTTT | 8.78 | 1457.2 [M − H]$^-$ | 8.80 | 1457.3 [M − H]$^-$ |
| TATAT | 7.75 | 1475.3 [M − H]$^-$ | 7.83 | 1475.4 [M − H]$^-$ |
| TGTGT | 7.07 | 1507.2 [M − H]$^-$ | 7.12 | 1507.3 [M − H]$^-$ |
| TTTTTTTTTT | 7.87 | 1488.5 [M − 2H]$^{2-}$ | 7.90 | 1488.7 [M − 2H]$^{2-}$ |
| ATATATATAT | 7.90 | 1511.0 [M − 2H]$^{2-}$ | 7.92 | 1511.2 [M − 2H]$^{2-}$ |
| CTCTCTCTCT | 7.63 | 1450.9 [M − 2H]$^{2-}$ | 7.58 | 1450.8 [M − 2H]$^{2-}$ |
| TACGTTACGT | 7.33 | 1507.6 [M − 2H]$^{2-}$ | 7.35 | 1507.5 [M − 2H]$^{2-}$ |

TABLE 8

Yields of Synthesised Oligonucleotides; Ester 40

| Oligonucleotide (DMTr-) | Synthetic Yields of Oligonucleotides (%) | | | | Ratio of stepwise yields: Photodirected/Conventional |
|---|---|---|---|---|---|
| | Photodirected | | Conventional | | |
| | Overall | Stepwise | Overall | Stepwise | |
| -(T)$_5$ | 79.5 | 94.4 | 82.3 | 95.2 | 0.991 |
| -TGTGT | 76.7 | 93.6 | 79.8 | 94.5 | 0.990 |
| -(T)$_{10}$ | 79.1 | 97.4 | 80.6 | 97.6 | 0.998 |

TABLE 8-continued

Yields of Synthesised Oligonucleotides; Ester 40

| Oligonucleotide (DMTr-) | Synthetic Yields of Oligonucleotides (%) | | | | Ratio of stepwise yields: Photodirected Conventional |
|---|---|---|---|---|---|
| | Photodirected | | Conventional | | |
| | Overall | Step-wise | Overall | Step-wise | |
| -(AT)$_5$ | 65.0 | 95.3 | 62.2 | 94.9 | 1.004 |
| -(CT)$_5$ | 73.4 | 96.6 | 72.3 | 96.4 | 1.002 |
| -(GT)$_5$ | 67.5 | 95.7 | 69.6 | 96.0 | 0.997 |
| -(TGCAT)$_2$ | 54.1 | 93.4 | 58.8 | 94.3 | 0.990 |

TABLE 9

Retention Times and Mass Spectra of Synthesised Oligonucleotides; Ester 40

| Oligonucleotide DMTr- | Retention Time* (min). Photodirected | Molecular Ion Observed. Photodirected | Retention Time* (min). Conventional | Molecular Ion Observed. Conventional |
|---|---|---|---|---|
| (T)$_5$ | 13.37 | 1759.4 [M − H]$^-$ | 13.37 | 1759.4 |
| TGTGT | 12.77 | 1809.3 [M − H]$^-$ | 12.78 | 1809.4 |
| (T)$_{10}$ | 12.85 | 1639.7 [M − 2H]$^{2-}$ | 12.90 | 1639.7 |
| (AT)$_5$ | 12.33 | 1662.4 [M − 2H]$^{2-}$ | 12.30 | 1662.0 |
| (CT)$_5$ | 12.25 | 1602.7 [M − 2H]$^{2-}$ | 12.30 | 1602.9 |
| (GT)$_5$ | 11.98 | 1702.0 [M − 2H]$^{2-}$ | 11.95 | 1702.0 |
| (TACGT)$_2$ | 12.35 | 1658.6 [M − 2H]$^{2-}$ | 12.38 | 1658.5 |

*0.05 M triethylammonium bicarbonate buffer/acetonitrile

SCHEME 1
SYNTHESIS OF PHOTOLABILE ESTERS

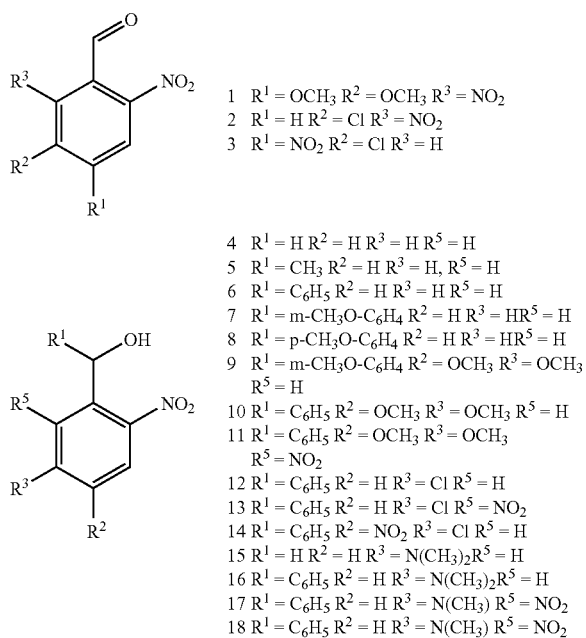

1  $R^1$ = OCH$_3$ $R^2$ = OCH$_3$ $R^3$ = NO$_2$
2  $R^1$ = H $R^2$ = Cl $R^3$ = NO$_2$
3  $R^1$ = NO$_2$ $R^2$ = Cl $R^3$ = H

4  $R^1$ = H $R^2$ = H $R^3$ = H $R^5$ = H
5  $R^1$ = CH$_3$ $R^2$ = H $R^3$ = H, $R^5$ = H
6  $R^1$ = C$_6$H$_5$ $R^2$ = H $R^3$ = H $R^5$ = H
7  $R^1$ = m-CH$_3$O-C$_6$H$_4$ $R^2$ = H $R^3$ = H $R^5$ = H
8  $R^1$ = p-CH$_3$O-C$_6$H$_4$ $R^2$ = H $R^3$ = H $R^5$ = H
9  $R^1$ = m-CH$_3$O-C$_6$H$_4$ $R^2$ = OCH$_3$ $R^3$ = OCH$_3$ $R^5$ = H
10 $R^1$ = C$_6$H$_5$ $R^2$ = OCH$_3$ $R^3$ = OCH$_3$ $R^5$ = H
11 $R^1$ = C$_6$H$_5$ $R^2$ = OCH$_3$ $R^3$ = OCH$_3$ $R^5$ = NO$_2$
12 $R^1$ = C$_6$H$_5$ $R^2$ = H $R^3$ = Cl $R^5$ = H
13 $R^1$ = C$_6$H$_5$ $R^2$ = H $R^3$ = Cl $R^5$ = NO$_2$
14 $R^1$ = C$_6$H$_5$ $R^2$ = NO$_2$ $R^3$ = Cl $R^5$ = H
15 $R^1$ = H $R^2$ = H $R^3$ = N(CH$_3$)$_2$ $R^5$ = H
16 $R^1$ = C$_6$H$_5$ $R^2$ = H $R^3$ = N(CH$_3$)$_2$ $R^5$ = H
17 $R^1$ = C$_6$H$_5$ $R^2$ = H $R^3$ = N(CH$_3$) $R^5$ = NO$_2$
18 $R^1$ = C$_6$H$_5$ $R^2$ = H $R^3$ = N(CH$_3$) $R^5$ = NO$_2$

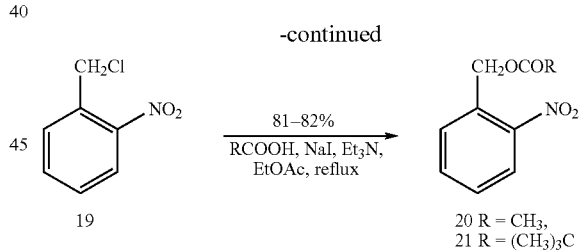

19 → 20 R = CH$_3$, 21 R = (CH$_3$)$_3$C
81–82% RCOOH, NaI, Et$_3$N, EtOAc, reflux

SCHEME 2
SYNTHESIS OF PHOTOLABILE ESTERS CONT.

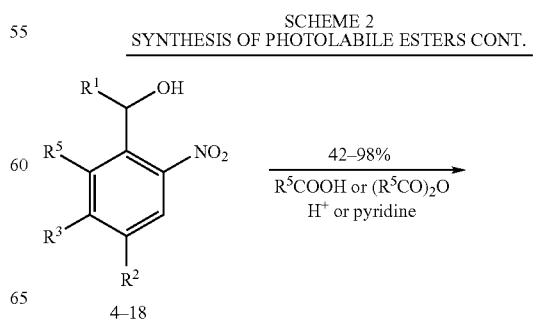

4–18 → 42–98% $R^5$COOH or ($R^5$CO)$_2$O H$^+$ or pyridine

-continued

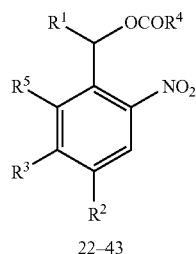

22–43

22 $R^1 = H\ R^2 = H\ R^3 = H\ R^4 = ClCH_2$
23 $R^1 = H\ R^2 = H\ R^3 = H\ R^4 = Cl_2CH$
24 $R^1 = H\ R^2 = H\ R^3 = H\ R^4 = CCl_3$
25 $R^1 = CH_3\ R^2 = H\ R^3 = H\ R^4 = CH_3$
26 $R^1 = CH_3\ R^2 = H\ R^3 = H\ R^4 = ClCH_2$
27 $R^1 = CH_3\ R^2 = H\ R^3 = H\ R^4 = Cl_2CH$
28 $R^1 = CH_3\ R^2 = H\ R^3 = H\ R^4 = CCl_3$
29 $R^1 = CH_3\ R^2 = H\ R^3 = H\ R^4 = (CH_3)_3C$
30 $R^1 = C_6H_5\ R^2 = H\ R^3 = H\ R^4 = CH_3$
31 $R^1 = C_6H_5\ R^2 = H\ R^3 = H\ R^4 = ClCH_2$
32 $R^1 = C_6H_5\ R^2 = H\ R^3 = H\ R^4 = Cl_2CH$
33 $R^1 = C_6H_5\ R^2 = H\ R^3 = H\ R^4 = CCl_3$
34 $R^1 = m\text{-}CH_3O\text{-}C_6H_4\ R^2 = H\ R^3 = H$
   $R^4 = ClCH_2$
35 $R^1 = m\text{-}CH_3O\text{-}C_6H_4\ R^2 = H\ R^3 = H$
   $R^4 = Cl_3C$
36 $R^1 = p\text{-}CH_3O\text{-}C_6H_4\ R^2 = H\ R^3 = H$
   $R^4 = Cl_2CH$
37 $R^1 = p\text{-}CH_3O\text{-}C_6H_4\ R^2 = H\ R^3 = H$
   $R^4 = Cl_3C$
38 $R^1 = m\text{-}CH_3O\text{-}C_6H_4\ R^2 = OCH_3\ R^3 = OCH_3$
   $R^4 = Cl_3C$
39 $R^1 = C_6H_5\ R^2 = OCH_3\ R^3 = OCH_3\ R^4 = Cl_3C$
40 $R^1 = C_6H_5\ R^2 = OCH_3,\ R^3 = OCH_3\ R^4 = Cl_3C$
41 $R^1 = H\ R^2 = H\ R^3 = N(CH_3)_2\ R^4 = Cl_3C$
42 $R^1 = C_6H_5\ R^2 = H\ R^3 = N(CH_3)_2\ R^4 = Cl_3C$
43 $R^1 = C_6H_5\ R^2 = H\ R^3 = N(CH_3)_2\ R^4 = Cl_3C$
44 $R^1 = H\ R^2 = H\ R^3 = N(CH_3)_2\ R^4 = Cl_3$

23–39, 41, 42 $R^5 = H$; 40, 43–44 $R^5 = NO_2$

Scheme 3
IRRADIATION OF PHOTOLABILE ESTERS

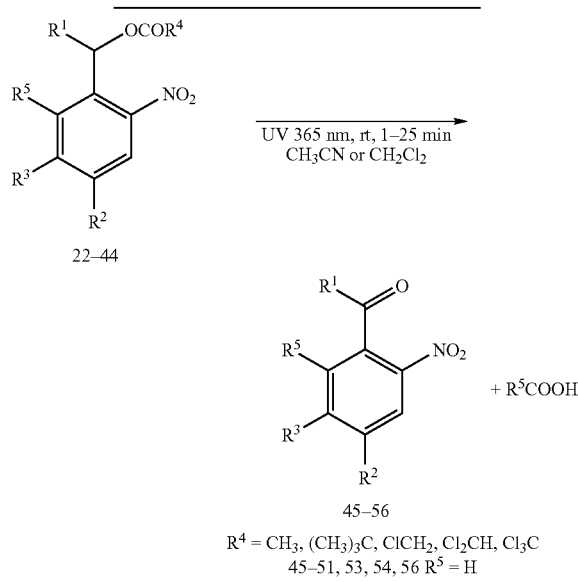

22–44

45–56

$R^4 = CH_3, (CH_3)_3C, ClCH_2, Cl_2CH, Cl_3C$
45–51, 53, 54, 56 $R^5 = H$

45 $R^1 = H\ R^2 = H\ R^3 = H$
46 $R^1 = CH_3\ R^2 = H\ R^3 = H$
47 $R^1 = C_6H_5\ R^2 = H\ R^3 = H$
48 $R^1 = m\text{-}CH_3O\text{-}C_6H_4\ R^2 = H\ R^3 = H$
49 $R^1 = p\text{-}CH_3O\text{-}C_6H_4\ R^2 = H\ R^3 = H$
50 $R^1 = m\text{-}CH_3O\text{-}C_6H_4\ R^2 = OCH_3\ R^3 = OCH_3$
51 $R^1 = C_6H_5\ R^2 = OCH_3\ R^3 = OCH_3$
52 $R^1 = C_6H_5\ R^2 = OCH_3\ R^3 = OCH_3\ R^5 = NO_2$
53 $R^1 = H\ R^2 = H\ R^3 = N(CH_3)_2$
54 $R^1 = C_6H_5\ R^2 = H\ R^3 = N(CH_3)_2$
55 $R^1 = C_6H_5\ R^2 = H\ R^3 = N(CH_3)_2\ R^5 = NO_2$
56 $R^1 = C_6H_5\ R^2 = NO_2\ R^3 = N(CH_3)_2\ R^5 = H$

REFERENCES

The references mentioned herein are all expressly incorporated by reference.

[1] Koshi & Shimizu, *Chem. Pharm. Bull.* 16(12), 2343-2350, 1968.
[2] Slotta & Lauersen, *Journal für Praktische Chemie*, 139, 220-228, 1934.
[3] Magnus & Westlund, *Tetrahedron Letters* 42, 2931-2932, 2001.
[4] Cunico, *Tetrahedron Letters* 42, 2931-2932, 2001.
[5] Corrie et al, *J. Chem. Soc. Perkin Transactions* 1, 1015-1019, 1992.
[6] Seebach et al, *Chem. Ber.* 3683-3699, 119, 1985.
[7] Puckowski & Ross, *J. Chem. Soc.* 3555-3558, 1959.
[8] Batey et al, *Organic Letters* 1683-1686, 1(10), 1999.
[9] Miyashita et al, *J. Chem. Soc. Perkin Trans.* 1, 1261-1268, 11, 1996.
[10] Effenberger & Spiegler, *Chem. Ber.* 3900-3914, 118, 1985.
[11] Smirnov et al, *Molecules* 4 (10), M113, 1999.
[12] Waksmundzka-Hajnos, *Acta Chromatographica*, 159-171, 7, 1997.
[13] Walser & Zenchoff, *J. Heterocyclic Chem.* 907-908, 13(4), 1976.
[14] Barzynski & Sanger, *Die Angewandte Makromolekulare Chemie* 131-141, 93, 1981.
[15] Colominas et al, *J. Chem. Soc. Perkin Transactions* 2, 997-1004, 1996.
[16] Yip et al, *J. Phys. Chem.* 5328-5230, 89(25), 1985.
[17] Reichmanis et al, *J. Polymer Science: Chemistry Edition* 1-8, 23, 1985.
[18] Urano et al, *Eur Pat. Appl.* 32 pp, EP 1991-307908.
[19] Barzynski et al, *Ger. Offen.*, 11 pp. DE 1972-2207574.
[20] Wharton et al, *Methods Enzymol.* 245-250, 291(Caged Compunds), 1998.
[21] Foot, *PCT Int. Appl.* 39 pp. WO 2000-US12131.
[22] Carlton & Royappa, *Nucleic Acids Research*, 3048-3052, 24 (15), 1996.
[23] Cummings & Krafft, *Tetrahedron Letters*, 65-68, 29, 1988.
[24] Walker et al, *J Am. Chem. Soc;.*, 7170-7177, 110, 1988.
[25] Kim et al, *J. Am. Chem. Soc* 5452-5456, 92, 1970.
[26] Cocker et al, *J Chem Soc* 751-756, 1938.
[27] Gao et al, *J. Am. Chem. Soc.* 12698-12699, 120, 1998.
[28] LeProust et al, *J. Comb. Chem.* 2, 349-354. 2000.
[29] Pease et al. *Proc. Natl. Acad. Sci.* (*USA*) 5022-5026, 91, 1994.
[30] McGall & Fidanza, "High Density Oligonucleotide Probe Arrays" in Adavances in Nucleic Acids and Protein Analysis, Manipulation and Sequencing" Limbach, P A et al eds. Proceedings of SPIE vol.3926 (2000), pp.106-110.

[31]Beecher et al, *Polymeric Materials Sci. Eng.* (Washington) 597-598, 76, 1997.

[32]Oligonucleotide Synthesis: A Practical Approach. IRL Press Ltd, Oxford, Washington D.C. 1984, Gait, M J; Editor.

[33]Oligonucleotides and Analogues: A Practical Approach. IRL Press Ltd, Oxford, New York, Tokyo, 1991, Eckstein, F; Editor.

[34]Reichmanis et al, *J. Polymer Science: Chemistry Edition* 1-8, 23, 1985.

[35]Caruthers, *Acc. Chem. Res*. 278-284, 24, 1991.

[36]Beaucage & Iyer, *Tetrahedron* 48, 2223-2311, 1992.

[37]Fodor et al, *Science* 251, 767-773, 1991.

[38]Singh-Gasson et al, *Nature Biotech*. 17, 974-978, 1999.

[39]Garner. Abstracts of Cambridge Healthtech Institute Conference "Lab Chips and Microarrays for Biotechnological Aplications", Zurich, 13-15 Jan., 1999.

[40]Staehler. Abstracts of IBC Conference "Chips to Hits", Philadelphia, 6-9 Nov., 2000.

[41]Hornbeck. Texas Instruments Tech. J. July-Sept, 7-46, 1998. (Obtainable at www.ti.com/dlp).

[42]Williams & Williams. "Basic Physical Chemistry for the Life Sciences", $2^{nd}$ Ed. 277-285. W. H Freeman & Co, San Francisco, 1973.

[43]Bevington. "Data Reduction and Error Analysis for the Physical Sciences" 27-37. McGraw-Hill Book Company, New York, 1969.

[44]Temsamani et al. *Nucleic Acids Res*. 23, 1841-1844, 1995.

[45]Fearon et al. *Nucleic Acids Res*. 23, 2754-2761, 1995.

The invention claimed is:

1. A compound represented by the formula:

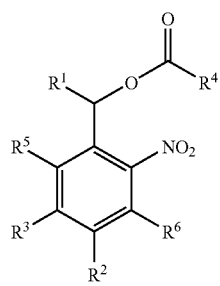

wherein:
$R^1$ is selected from aryl or alkoxy-substituted aryl, or aryloxy or substituted aryloxy;
$R^2$ is selected from hydrogen, halogen, alkyl or substituted alkyl, alkoxy or substituted alkoxy, aryl or substituted aryl, aryloxy or substituted aryloxy, amino or substituted amino or a nitro group;
$R^3$ is selected from hydrogen, alkoxy or substituted alkoxy, aryl or substituted aryl, aryloxy or substituted aryloxy, amino or substituted amino, or an unsubstituted or substituted heterocyclic group;
$R^4$ is an alkyl group substituted with one or more halogen substituents;
$R^5$ is selected from hydrogen, halogen, alkyl or substituted alkyl, alkoxy or substituted alkoxy, aryl or substituted aryl, aryloxy or substituted aryloxy, amino or substituted amino, a nitro group or an unsubstituted or substituted heterocyclic group; and,
$R^6$ is selected from hydrogen, halogen, alkyl or substituted alkyl, alkoxy or substituted alkoxy, aryl or substituted aryl, aryloxy or substituted aryloxy, or amino or substituted amino, or an unsubstituted or substituted heterocyclic group.

2. The compound of claim 1, wherein $R^4$ is $ClCH_2$, $Cl_2CH$, $Cl_3C$ or $F_3C$.

3. The compound of claim 1 wherein:
$R^1$ is a phenyl or alkoxy substituted phenyl group, a 3-alkoxy substituted phenyl group; and/or,
$R^2$ is hydrogen or a substituted or unsubstituted alkoxy group; and/or,
$R^3$ is hydrogen, a substituted or unsubstituted alkoxy group or an amino or substituted amino group; and/or,
$R^4$ is $ClCH_2$, $CL_2CH$, $Cl_3C$ or $F_3C$; and/or,
$R^5$ is hydrogen or a nitro group; and/or
$R^6$ is hydrogen.

4. The compound of claim 1, wherein:
$R^1$ is $C_6H5$, m-$CH_3O$—$C_6H_4$, or p-$CH_3O$—$C_6H_4$; and/or
$R^2$ is hydrogen or $OCH_3$; and/or,
$R^3$ is hydrogen, $OCH_3$ or $N(CH_3)_2$; and/or,
$R^4$ is $ClCH_2$, $Cl_2CH$, $Cl_3C$ or $F_3C$; and/or
$R^5$ is hydrogen or a nitro group; and/or
$R^6$ is hydrogen.

5. The compound of claim 1, wherein the compound is trichloroacetic acid (4,5-dimethoxy-2-nitro-phenyl)-phenyl-methyl ester (39); or trichloroacetic acid (4,5-dimethoxy-2,6-dinitro-phenyl)-phenyl-methyl ester (40), or trichloroacetic acid (5-dimethylamino-2,6-dinitro-phenyl)-phenyl-methyl ester (43).

6. A polymeric film that comprises a compound according to claim 1.

7. A method of synthesizing a nucleic acid molecule or peptide on a solid support, the method comprising:
(a) bringing a nucleic acid molecule or peptide having a protected terminus into contact with a compound having a formula as defined in claim 1
(b) photolysing the compound to produce a halogen substituted carboxylic acid capable of removing the protecting group from the end of the nucleic acid molecule or peptide;
(c) contacting the deprotected nucleic acid molecule or peptide with nucleosides or amino acids, so that the 5' end of the nucleic acid molecule or peptide reacts with a nucleoside or amino acid; and
(d) repeating steps (a) to (c) until the synthesis of the nucleic acid molecule or peptide is complete.

8. The method of claim 7, wherein the halogen substituted acid generated by the photolysis of the compound is capable of removing a 5'-O-dimethoxytrityl (DMT) protecting group present on the 5' end of a nucleic acid molecule or peptide.

9. The method of claim 7 wherein the compounds are used in the synthesis of an array having a plurality of array elements, wherein a nucleic acid molecule or peptide is synthesized at each element of the array.

10. The method of claim 7, wherein the nucleic acid molecules or peptides are synthesised on a glass surface.

11. The method of claim 7, photolysing the compounds is carried out by projection lithography.

12. The method of claim 7, the compounds are immobilized in a solid polymer film to prevent or reduce acid diffusion from irradiated to non-irradiated array elements.

13. The method of claim 7, wherein a base or a buffer is provided at each element in the array to neutralise acid generated by stray light photolysing the compound present at elements of the array other than those elements targeted for synthesis.

14. The method of claim 7, wherein the compounds are capable of being photolysed by visible light.

15. The method of claim 11, wherein the projection lithography is maskless projection lithography.

* * * * *